(12) United States Patent
Lee et al.

(10) Patent No.: US 10,349,918 B2
(45) Date of Patent: Jul. 16, 2019

(54) METHOD AND APPARATUS FOR DISPLAYING ULTRASOUND IMAGES

(71) Applicant: SAMSUNG MEDISON CO., LTD., Hongcheon-gun (KR)

(72) Inventors: Bong-heon Lee, Hongcheon-gun (KR); Dong-kuk Shin, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 73 days.

(21) Appl. No.: 15/196,574

(22) Filed: Jun. 29, 2016

(65) Prior Publication Data

US 2017/0172545 A1    Jun. 22, 2017

(30) Foreign Application Priority Data

Dec. 22, 2015    (KR) .......................... 10-2015-0184080

(51) Int. Cl.
*G16H 50/70*    (2018.01)
*G06F 17/21*    (2006.01)
*G06F 3/0484*    (2013.01)
*A61B 6/00*    (2006.01)
(Continued)

(52) U.S. Cl.
CPC .............. *A61B 8/463* (2013.01); *A61B 6/463* (2013.01); *A61B 8/00* (2013.01); *A61B 8/485* (2013.01);
(Continued)

(58) Field of Classification Search
CPC ....... A61B 8/5207; A61B 8/469; A61B 8/463; A61B 8/14; A61B 8/4483; A61B 8/488; A61B 8/465; A61B 8/00; A61B 8/52; A61B 8/5223; A61B 8/5215; A61B 8/5238; A61B 8/54; A61B 8/13; A61B 6/469; A61B 6/463; A61B 2090/378; A61B 5/743; G06T 2207/10132; G06T 2207/20104; G06T 2207/30004; G06T 7/0012; G06T 7/174; G06T 2210/41; G06F 19/321; G06F 3/04817; G06F 3/0482; G06F 17/212; G06F 17/24; G06F 3/04842; G16H 10/60; G16H 15/00; G16H 50/70; G16H 50/20; G16H 30/00; G16H 30/40; G06K 2209/05;
(Continued)

(56) References Cited

U.S. PATENT DOCUMENTS 6,254,540 B1 *  7/2001  Kikuchi .................. A61B 8/00
                                                128/916
7,676,379 B2    3/2010  Kil et al.
(Continued)

FOREIGN PATENT DOCUMENTS

JP    2013-169212 A    9/2013
KR   10-2007-0033340 A   3/2007
KR   10-2015-0006807 A   1/2015

OTHER PUBLICATIONS

Communication dated May 11, 2017 by the European Patent Office in counterpart European Patent Application No. 16184051.7.

Primary Examiner — Dismery Mercedes
(74) Attorney, Agent, or Firm — Sughrue Mion, PLLC

(57) ABSTRACT

Provided is a method of displaying a medical image, including: generating a first image showing a region of interest (ROI) by using echo signals corresponding to ultrasound signals transmitted toward the ROI; selecting second images showing the ROI from among prestored images; and displaying the first image and the second images on a screen.

17 Claims, 18 Drawing Sheets

(51) Int. Cl.
*A61B 8/00* (2006.01)
*G06T 7/00* (2017.01)
*A61B 8/08* (2006.01)
*G16H 15/00* (2018.01)
*G01S 7/52* (2006.01)
*G06T 7/30* (2017.01)
*G06T 7/11* (2017.01)
*G16H 30/40* (2018.01)
*G16H 10/60* (2018.01)
*G06F 17/24* (2006.01)
*G01S 15/89* (2006.01)

(52) U.S. Cl.
CPC ............ *A61B 8/488* (2013.01); *A61B 8/5223* (2013.01); *G01S 7/52063* (2013.01); *G01S 7/52073* (2013.01); *G01S 7/52074* (2013.01); *G06F 3/04842* (2013.01); *G06F 17/212* (2013.01); *G06T 7/0012* (2013.01); *G06T 7/11* (2017.01); *G06T 7/30* (2017.01); *G16H 15/00* (2018.01); *G16H 50/70* (2018.01); *A61B 8/4405* (2013.01); *G01S 7/52036* (2013.01); *G01S 15/8915* (2013.01); *G06F 17/24* (2013.01); *G06T 2207/10132* (2013.01); *G06T 2207/30004* (2013.01); *G16H 10/60* (2018.01); *G16H 30/40* (2018.01)

(58) Field of Classification Search
CPC ............ G06K 9/6292; G06K 9/6211; G06K 9/00147; G01S 7/52036; G01S 7/52063; G01S 7/52074
See application file for complete search history.

(56) References Cited

U.S. PATENT DOCUMENTS

| | | | |
|---|---|---|---|
| 8,280,129 B2 | 10/2012 | Futami et al. | |
| 8,600,133 B2* | 12/2013 | Buelow | G06T 7/0012 382/128 |
| 9,177,110 B1* | 11/2015 | Fram | G06F 19/321 |
| 9,642,601 B2* | 5/2017 | Shin | A61B 8/463 |
| 9,901,300 B2* | 2/2018 | Koh | A61B 5/4887 |
| 9,905,006 B2* | 2/2018 | Zhu | G06T 7/0014 |
| 2004/0151358 A1* | 8/2004 | Yanagita | G06F 19/321 382/132 |
| 2005/0259116 A1* | 11/2005 | Araoka | A61B 6/463 345/619 |
| 2007/0237377 A1* | 10/2007 | Oosawa | G06F 19/321 382/128 |
| 2007/0242069 A1* | 10/2007 | Matsue | G06F 19/321 345/428 |
| 2008/0004520 A1* | 1/2008 | Theriault | A61B 5/055 600/410 |
| 2009/0080734 A1* | 3/2009 | Moriya | G06F 19/321 382/128 |
| 2010/0179427 A1* | 7/2010 | Yamamoto | A61B 8/00 600/443 |
| 2013/0070993 A1* | 3/2013 | Baek | A61B 8/463 382/131 |
| 2013/0253953 A1* | 9/2013 | Hisanaga | G06Q 50/24 705/3 |
| 2013/0324849 A1* | 12/2013 | Park | A61B 8/463 600/440 |
| 2014/0301665 A1* | 10/2014 | Saito | G06F 19/321 382/299 |
| 2014/0378836 A1 | 12/2014 | Lee | |
| 2015/0011872 A1 | 1/2015 | Koh et al. | |
| 2015/0015612 A1* | 1/2015 | Kurosaki | G16H 15/00 345/636 |
| 2015/0209013 A1 | 7/2015 | Tsymbalenko | |
| 2015/0305718 A1* | 10/2015 | Ogasawara | A61B 8/461 600/440 |
| 2016/0125162 A1* | 5/2016 | Takata | G06F 19/321 705/2 |
| 2016/0217576 A1* | 7/2016 | Kabus | A61B 6/469 |
| 2016/0335394 A1* | 11/2016 | Kawagishi | G06F 19/321 |
| 2017/0011187 A1* | 1/2017 | Oosawa | A61B 6/00 |

* cited by examiner

FIG. 18A
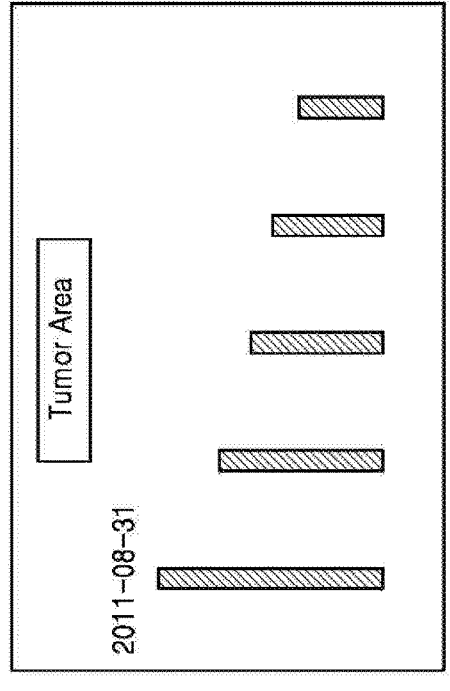
FIG. 18B
FIG. 18C
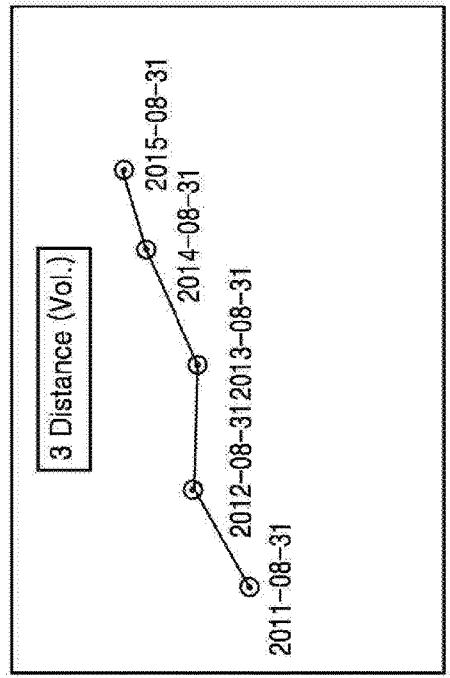
FIG. 18D
| | 2011-08 | 2012-08 | 2013-08 | 2014-08 | 2015-08 |
|---|---|---|---|---|---|
| measurement 1 | 88.235 | 40.4517 | 57.06005 | 5.151227 | 69.21944 |
| measurement 2 | 92.95219 | 46.2977 | 47.94677 | 33.1239 | 48.10357 |
| measurement 3 | 95.16844 | 44.07981 | 40.74034 | 56.28862 | 36.55781 |
| measurement 4 | 74.20378 | 8.382523 | 48.01769 | 10.76682 | 65.15684 |
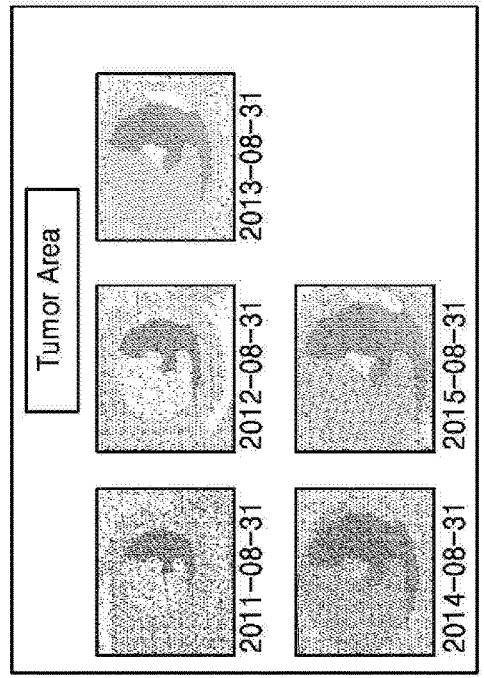

METHOD AND APPARATUS FOR DISPLAYING ULTRASOUND IMAGES

CROSS-REFERENCE TO RELATED APPLICATION

This application claims the benefit of Korean Patent Application No. 10-2015-0184080, filed on Dec. 22, 2015, in the Korean Intellectual Property Office, the disclosure of which is incorporated herein in its entirety by reference.

BACKGROUND

1. Field

The present disclosure relates to methods and apparatuses for displaying ultrasound images.

2. Description of the Related Art

Ultrasound diagnosis apparatuses transmit ultrasound signals generated by transducers of a probe to an object and receive echo signals reflected from the object, thereby obtaining at least one image of an object or an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

SUMMARY

Provided are methods and apparatuses for displaying ultrasound images.

Provided are non-transitory computer-readable recording media having recorded thereon programs for executing the methods of displaying ultrasound images on a computer.

Additional aspects will be set forth in part in the description which follows and, in part, will be apparent from the description, or may be learned by practice of the presented embodiments.

According to an aspect of an embodiment, a method of displaying a medical image includes: generating a first image showing a region of interest (ROI) by using echo signals corresponding to ultrasound signals transmitted toward the ROI; selecting second images showing the ROI from among prestored images; and displaying the first image and the second images on a screen.

The displaying of the first image and the second images on the screen may include: displaying thumbnail images corresponding to the second images in a region of the screen; and displaying images that are most similar to the first image from among the second images in a region of the screen other than the region where the thumbnail images are displayed.

The displaying of the first image and the second images on the screen may include: displaying thumbnail images corresponding to the second images in a region of the screen; and displaying an image selected based on a user input from among the second images in a region of the screen other than the region where the thumbnail images are displayed.

The displaying of the first image and the second images on the screen may include displaying the second images in different regions into which the screen is partitioned, based on at least one time point when the second images are generated.

The at least one time point may include at least one time point selected based on a user input from among time points when the prestored images are generated.

The displaying of the first image and the second images on the screen may include aligning the second images based on time points when the second images are generated to thereby display the aligned second images.

The displaying of the first image and the second images on the screen may include displaying an image that is most similar to the first image from among the second images in such a manner that the most similar image is distinguished from the other ones among the second images.

The selecting of the second images may include selecting, from among the prestored images, images on which the same parameter as a parameter measured based on the first image is measured, as the second images.

The selecting of the second images may include selecting, from among the prestored images, images generated under the same conditions as those used to generate the first image.

According to an aspect of another embodiment, a non-transitory computer-readable recording medium has recorded thereon a program for executing the method on a computer.

According to an aspect of another embodiment, an apparatus for displaying a medical image includes: an image processor configured to generate a first image showing an ROI by using echo signals corresponding to ultrasound signals transmitted toward the ROI; a controller configured to select second images showing the ROI from among prestored images; and a display configured to display the first image and the second images on a screen in response to a control signal generated by the controller.

The controller may generate the control signal so that thumbnail images corresponding to the second images are displayed in a region of the screen while images that are most similar to the first image among the second images are displayed in a region of the screen other than the region where the thumbnail images are displayed.

The controller may generate the control signal so that thumbnail images corresponding to the second images are displayed in a region of the screen while an image selected based on a user input from among the second images is displayed in a region of the screen other than the region where the thumbnail images are displayed.

The controller may generate the control signal so that the second images are displayed in different regions into which the screen is partitioned, based on at least one time point when the second images are generated.

The at least one time point may include at least one time point selected based on a user input from among time points when the prestored images are generated.

The controller may generate the control signal so that the second images are aligned based on time points when the second images are generated and displayed.

The controller may generate the control signal so that an image that is most similar to the first image from among the second images is displayed in such a manner that the most similar image is distinguished from the other ones among the second images.

The controller may select, from among the prestored images, images on which the same parameter as a parameter measured based on the first image is measured, as the second images.

The controller may select, from among the prestored images, images generated under the same conditions as those used to generate the first image.

BRIEF DESCRIPTION OF THE DRAWINGS

These and/or other aspects will become apparent and more readily appreciated from the following description of the embodiments, taken in conjunction with the accompanying drawings in which:

FIGS. 18A through 18D illustrate examples in which measured values of a parameter are output on a screen, according to an embodiment.

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention. Expressions such as "at least one of," when preceding a list of elements, modify the entire list of elements and do not modify the individual elements of the list.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves or an image showing a region of interest (ROI) included in the object. An ROI refers to a region of an object that a user desires to observe with more focused attention, and, for example, may be a region including a lesion. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments will be described in detail with reference to the accompanying drawings.

Figure 1A:
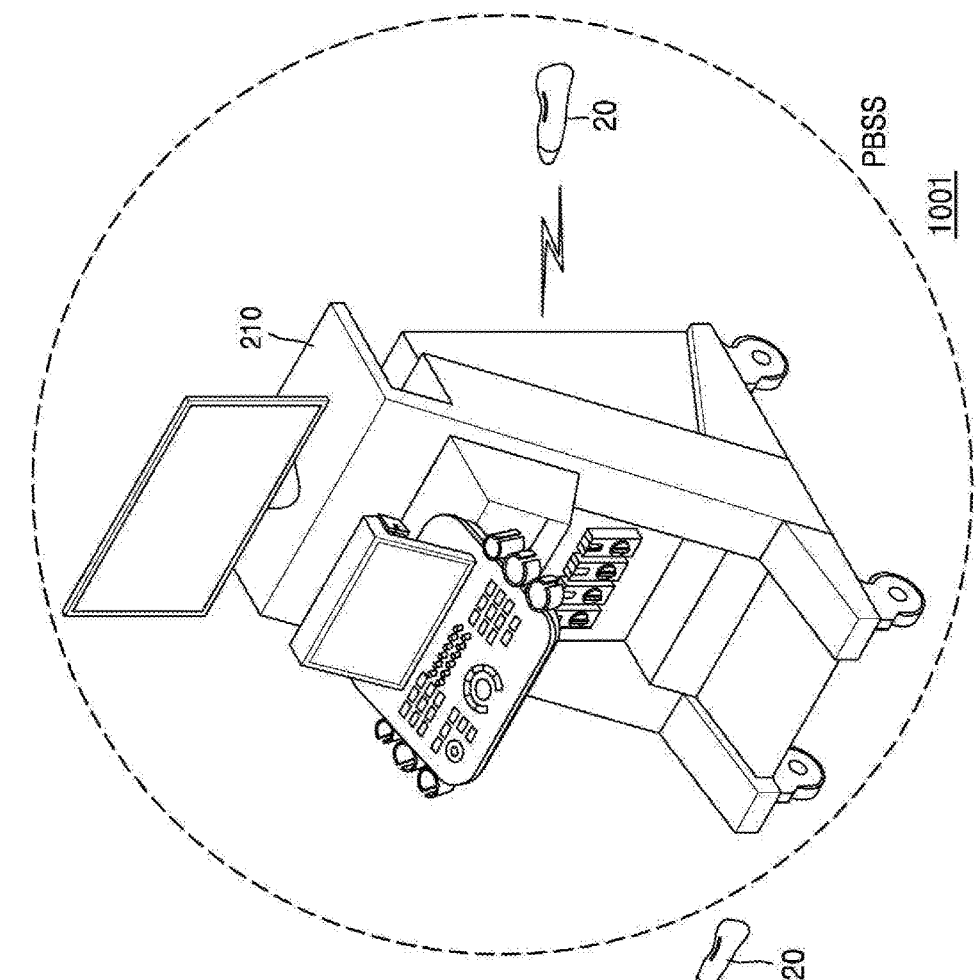
FIGS. 1A and 1B illustrate examples of ultrasound diagnosis systems according to embodiments.
Figure 1B:
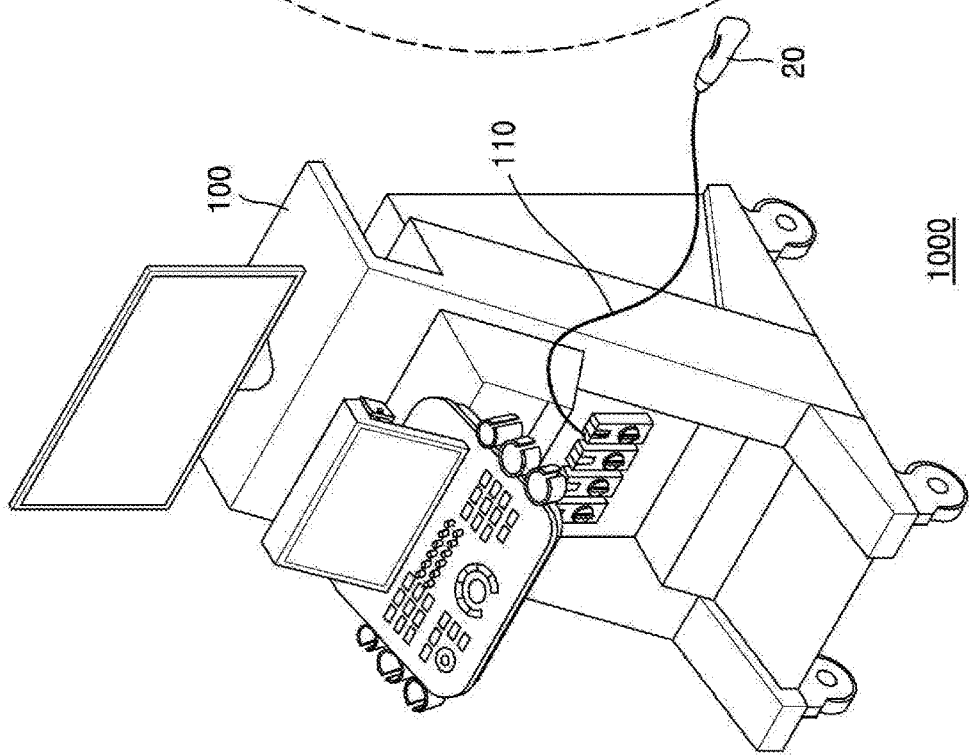

FIGS. 1A and 1B are diagrams showing examples of ultrasound diagnosis systems 1000 and 1001 according to embodiments.

FIGS. 1A and 1B are diagrams showing examples of ultrasound diagnosis systems 1000 and 1001 according to embodiments.

Referring to FIG. 1A, in the ultrasound diagnosis system 1000, a probe 20 may be connected by wire to an ultrasound imaging apparatus 100. In other words, the probe 20 for transmitting and receiving ultrasound waves may be connected to a main body of the ultrasound diagnosis system 1000, i.e., the ultrasound imaging apparatus 100 via a cable 110.

Referring to FIG. 1B, in the ultrasound diagnosis system 1001, a probe 20 may be connected wirelessly to an ultrasound imaging apparatus 210. In other words, the probe 20 may be connected to the ultrasound imaging apparatus 210 via the same wireless network. For example, the probe 20 and the ultrasound imaging apparatus 210 may be combined with a Millimeter Wave (mmWave) based wireless network, and the probe 20 may transmit echo signals received through transducers to the ultrasound imaging apparatus 210 in the 60 GHz frequency band. The ultrasound imaging apparatus 210 may generate ultrasound images via various imaging modalities by using echo signals received in the 60 GHz frequency band and display the generated ultrasound images. In this case, the mmWave based wireless network may use a wireless communication method compliant with the WiGig standard developed by Wireless Gigabit Alliance (WGA), but is not limited thereto FIG. 2 is a block diagram of a configuration of an ultrasound diagnosis system 1002 according to an embodiment.

Figure 2:
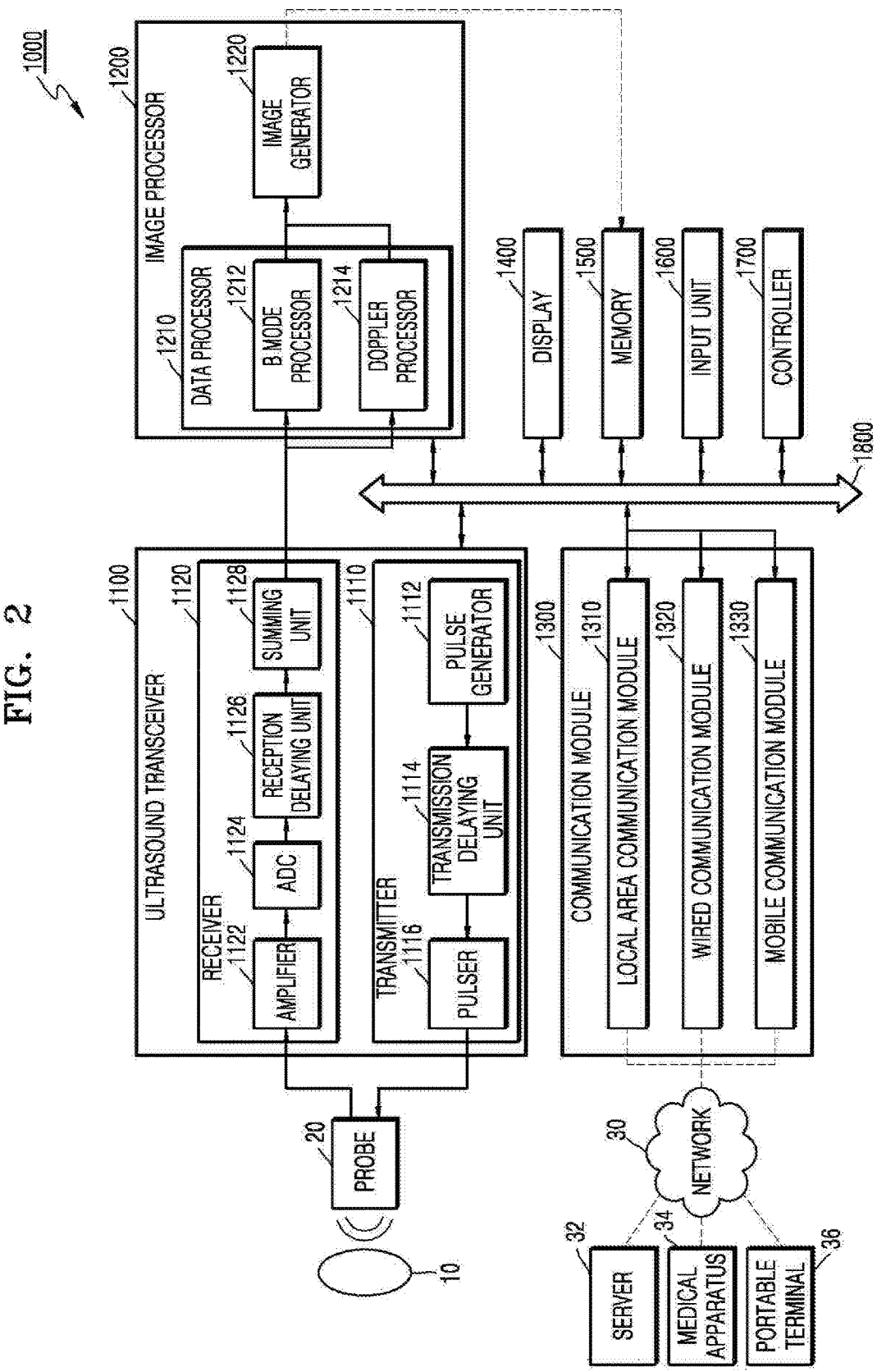
FIG. 2 is a diagram of a configuration of an ultrasound diagnosis system according to an embodiment.

Referring to FIG. 2, the ultrasound diagnosis system 1002 may include a probe 20 and an ultrasound imaging apparatus 100. Here, the ultrasound imaging apparatus 100 may include an ultrasound transceiver 1100, an image processor 1200, a communication module 1300, a display 1400, a memory 1500, an input unit 1600, and a controller 1700, which may be connected to one another via buses 1800.

The ultrasound diagnosis system 1002 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound signals to an object 10 (or to an ROI in the object 10) in response to a driving signal applied by the ultrasound transceiver 1100 and receives echo signals reflected by the object 10 (or by the ROI in the object 10). The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis system 1002 by wire or wirelessly, and according to embodiments, the ultrasound diagnosis system 1002 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound imaging apparatus 1002 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. Furthermore, when the probe 20 is connected to the ultrasound imaging apparatus 1002 via a wireless network, the communication module 1300 may communicate with the probe 20.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object 10, such as ultrasound data and an ultrasound image that are input or output, and may also store algorithms or programs which are to be executed in the ultrasound imaging apparatus 1002.

The memory 1500 may be any of various storage media, e.g., a flash memory, a hard disk drive, EEPROM, etc. Furthermore, the ultrasound imaging apparatus 1002 may utilize web storage or a cloud server that performs the storage function of the memory 1500 online.

The input unit 1600 refers to a unit via which a user inputs data for controlling the ultrasound imaging system 1002. The input unit 1600 may include hardware components, such as a keyboard, a mouse, a touch pad, a touch screen, a trackball, and a jog switch, and software modules for operating the hardware components. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, embodiments of the present invention are not limited thereto.

Figure 3:
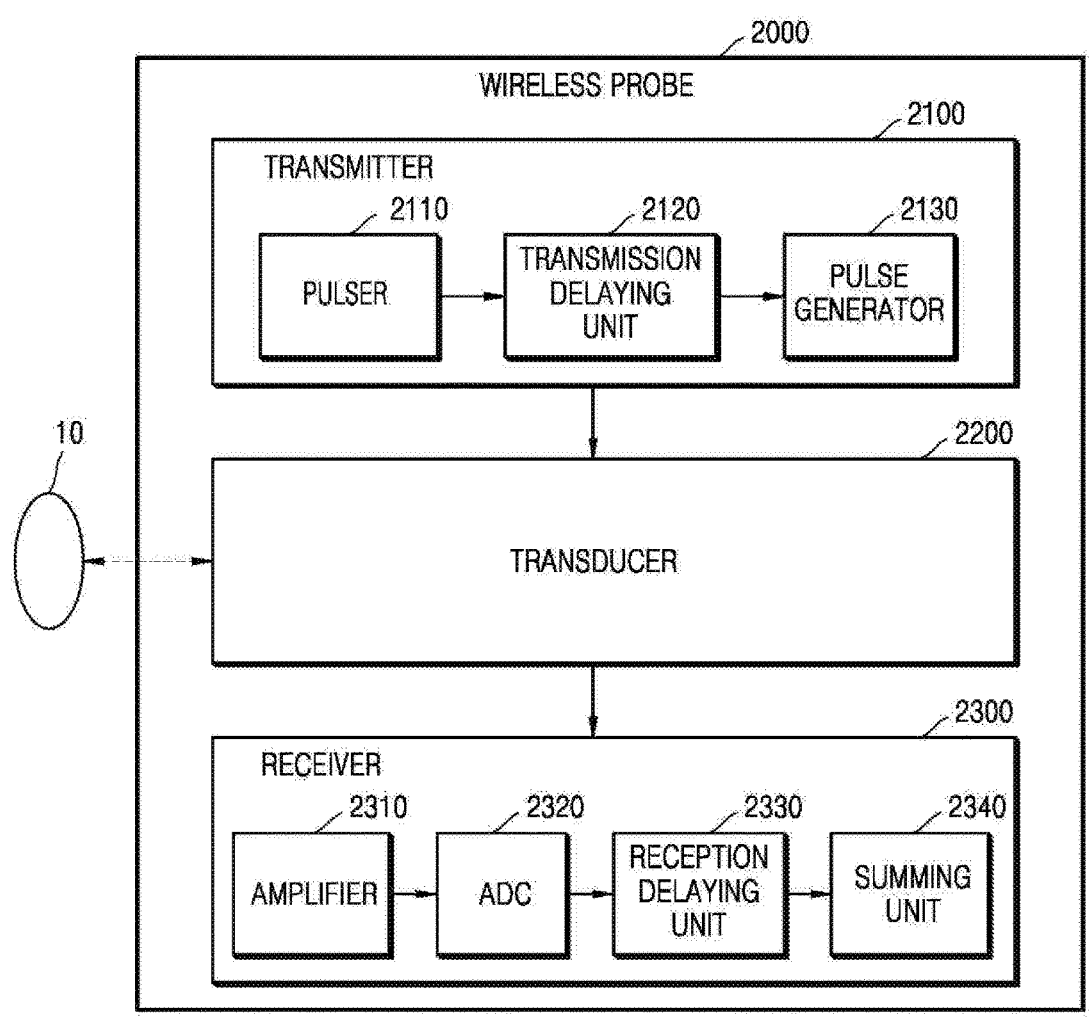
FIG. 3 is a diagram of a configuration of a wireless probe according to an embodiment.

FIG. 3 is a diagram showing a wireless probe 2000 according to an embodiment.

Referring to FIG. 3, as described above with reference to FIG. 2, the wireless probe 2000 may include a plurality of transducers, and, according to embodiments, may include some or all of the components of the ultrasound transceiver 1100 shown in FIG. 2.

The wireless probe 2000 according to the embodiment shown in FIG. 2 includes a transmitter 2100, a transducer 2200, and a receiver 2300. Since descriptions thereof are given above with reference to FIG. 2, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound imaging apparatus 1002 shown in FIG. 2.

Figure 4A:
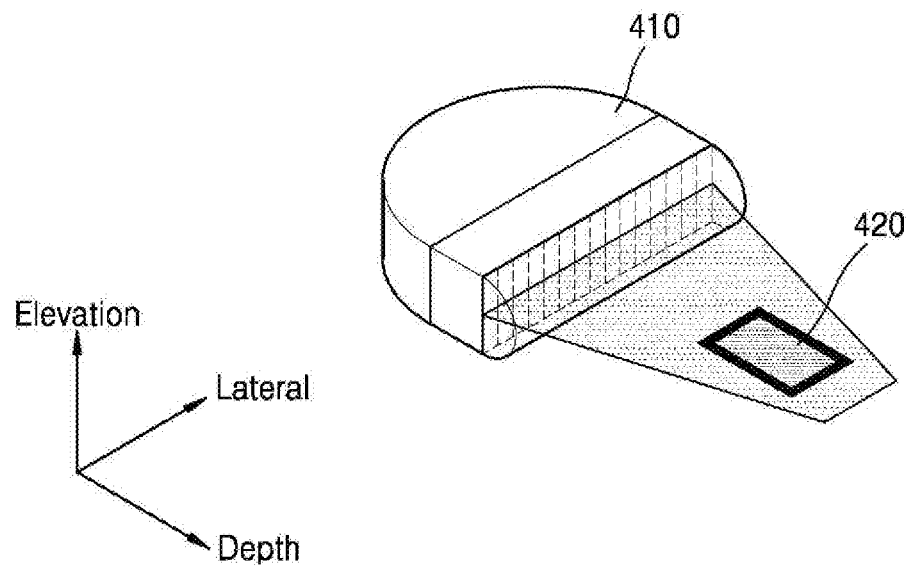
FIGS. 4A and 4B illustrate examples in which a probe transmits ultrasound signals to an object, according to an embodiment.
Figure 4B:
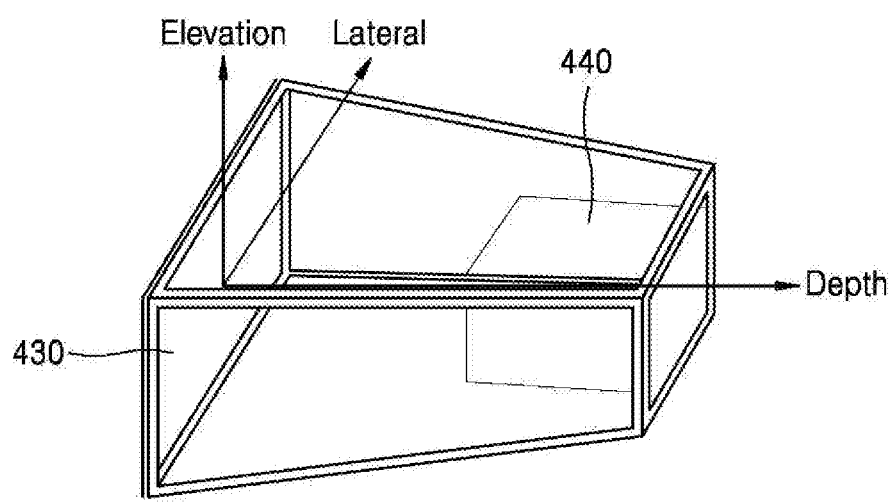

FIGS. 4A and 4B illustrate examples in which a probe transmits ultrasound signals to an object, according to an embodiment.

Probes 410 and 430 respectively shown in FIGS. 4A and 4B may correspond to the probe 20 shown in FIG. 1A, or the probe 20 and the wireless probe 2000 respectively shown in FIGS. 1B and 3.

Referring to FIG. 4A, the probe 410 may be formed by a one-dimensional (1D) array of a plurality of transducers. In this case, the transducers are elements constituting the probe 410 and transmit ultrasound signals to an object 420 and receive echo signals reflected from the object 420. The plurality of transducers oscillate in response to reflected echo signals, generate electrical pulses corresponding to the oscillations, and output the electrical pulses to the ultrasound transceiver 1100.

Furthermore, transducers in the probe 410 may constitute an aperture or sub-array. In this case, the aperture is a set of some of the plurality of transducers in the probe 410. The number of transducers that constitute an aperture is not limited to a specific number, and one aperture may be composed of a single transducer.

Furthermore, referring to FIG. 4B, the probe 430 may be formed by a 2D array of a plurality of transducers. The probe 430 may transmit ultrasound signals to a 3D object 440 and receive echo signals reflected from the object 440. In this case, the probe 430 may transmit ultrasound signals to the object 440 and receive echo signals in the same manner as described with reference to FIG. 4A.

Figure 5:
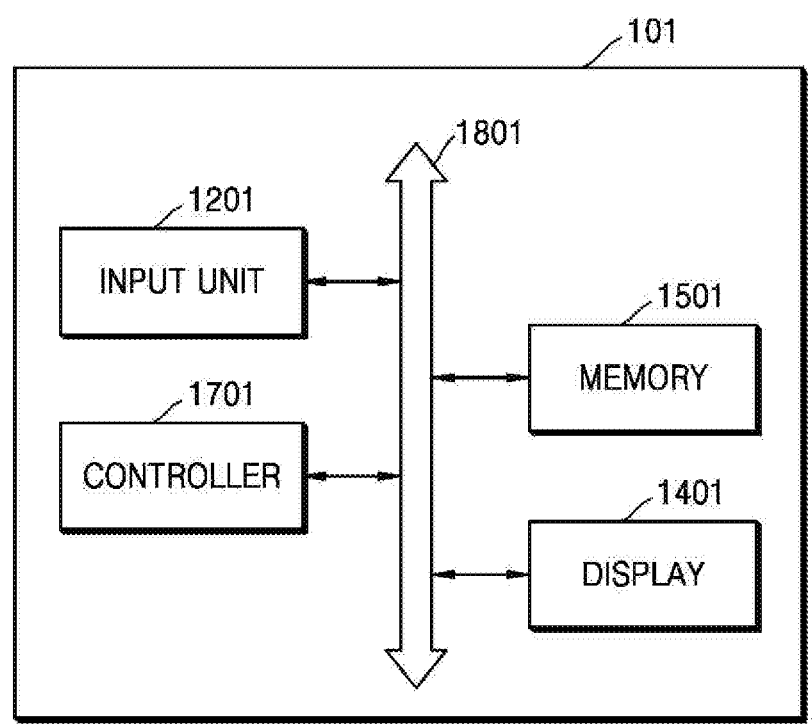
FIG. 5 is a diagram of a configuration of a display apparatus for displaying a medical image according to an embodiment.

FIG. 5 is a diagram of a configuration of a display apparatus 101 for displaying a medical image according to an embodiment.

Referring to FIG. 5, the display apparatus 101 includes an image processor 1201, a display 1401, and a memory 1501, and a controller 1701, all of which are connected to one another via a bus 1801. In this case, all or some of the image processor 1201, the display 1401, the memory 1501, and the controller 1701 may be implemented using software modules, but are not limited thereto. Some of the components may also be implemented as hardware modules. Furthermore, each of the image processor 1201, the display 1401, and the input unit 1601 may include an independent control module.

The display apparatus 101 displays a first image generated by the image processor 1201 and at least one second image read from the memory 1501 on a screen. For example, the display 1401 may display second images showing the same ROI (e.g., the same application, etc.) as an ROI shown in the first image, together with the first image. Furthermore, the display 1401 may display, together with the first image, second images on which a same parameter (e.g., a size, a volume, a length, etc.) as a parameter measured by a user based on the first image is measured. Furthermore, the display 1401 may display, together with the first image, second images generated under the same conditions as those used to generate the first image (e.g., probe type, time gain compensation (TGC)/lateral gain compensation (LGC) values, depth, etc.).

Thus, the user may determine how an ROI changes over time based on images displayed by the display apparatus 101. Furthermore, the display apparatus 101 may automatically select an image similar to a currently captured image from among prestored images and display the automatically selected image, thus reducing the amount of time that it takes for a user to diagnose an object based on the image.

Examples in which the display apparatus 1001 displays a first image and second images on a single screen will be described in more detail below with reference to FIGS. 6 through 18.

Figure 6:
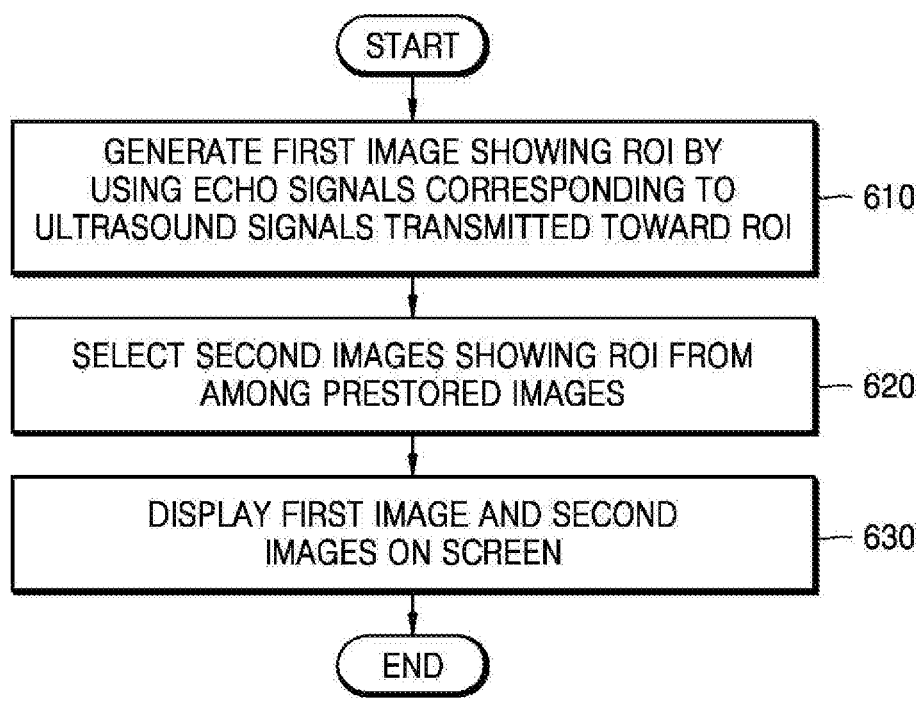
FIG. 6 is a flowchart of an example of a method of displaying a medical image according to an embodiment.

FIG. 6 is a flowchart of an example of a method of displaying a medical image according to an embodiment.

Referring to FIG. 6, the method of displaying a medical image includes operations sequentially performed by the ultrasound diagnosis systems 1000, 1001, and 1002 of FIGS. 1A, 1B, and 2 or the display apparatus 101 of FIG. 5. Thus, although omitted hereinafter, the descriptions with respect to the ultrasound diagnosis systems 1000, 1001, and 1002 of FIGS. 1A, 1B, and 2 or the display apparatus 101 of FIG. 5 apply to the method of FIG. 6.

The image processor 1201 generates at least one first image showing an ROI by using echo signals corresponding to ultrasound signals transmitted toward the ROI (operation 610). In this case, the ROI refers to a target inside an object that a user desires to observe, and, for example, may include a lesion or an internal tissue of the object. The image processor 1201 generates at least one first image in the same manner as described above with reference to FIG. 2.

The controller 1701 selects second images showing an ROI from among images prestored in the memory 1501 (operation 620). In this case, the second images mean images that are read by the controller 1701 from the memory 1501 from among images stored in the memory 1501. A plurality of medical images generated by the image processor 1201 may be stored in the memory 1501. In other words, captured medical images of various objects may be stored in the memory 1501. The controller 1701 may read captured medical images of an object that is a target contained in the first image from among the medical images stored in the memory 1501. For example, the controller 1701 may select and read captured images of the same ROI as an ROI shown in the first image from among captured images of the object stored in the memory 1501. As another example, the controller 1701 may select and read, from among captured images of the object stored in the memory 1501, images on which the same parameter as a parameter measured by the user based on the first image is measured. As another example, the controller 1701 may select and read, from among captured images of the object stored in the memory 1501, images generated under the same conditions as s those used to generate the first image Examples in which the controller 1701 selects second images from among images stored in the memory 1501 will now be described with reference to FIGS. 7 through 9.

Figure 7:
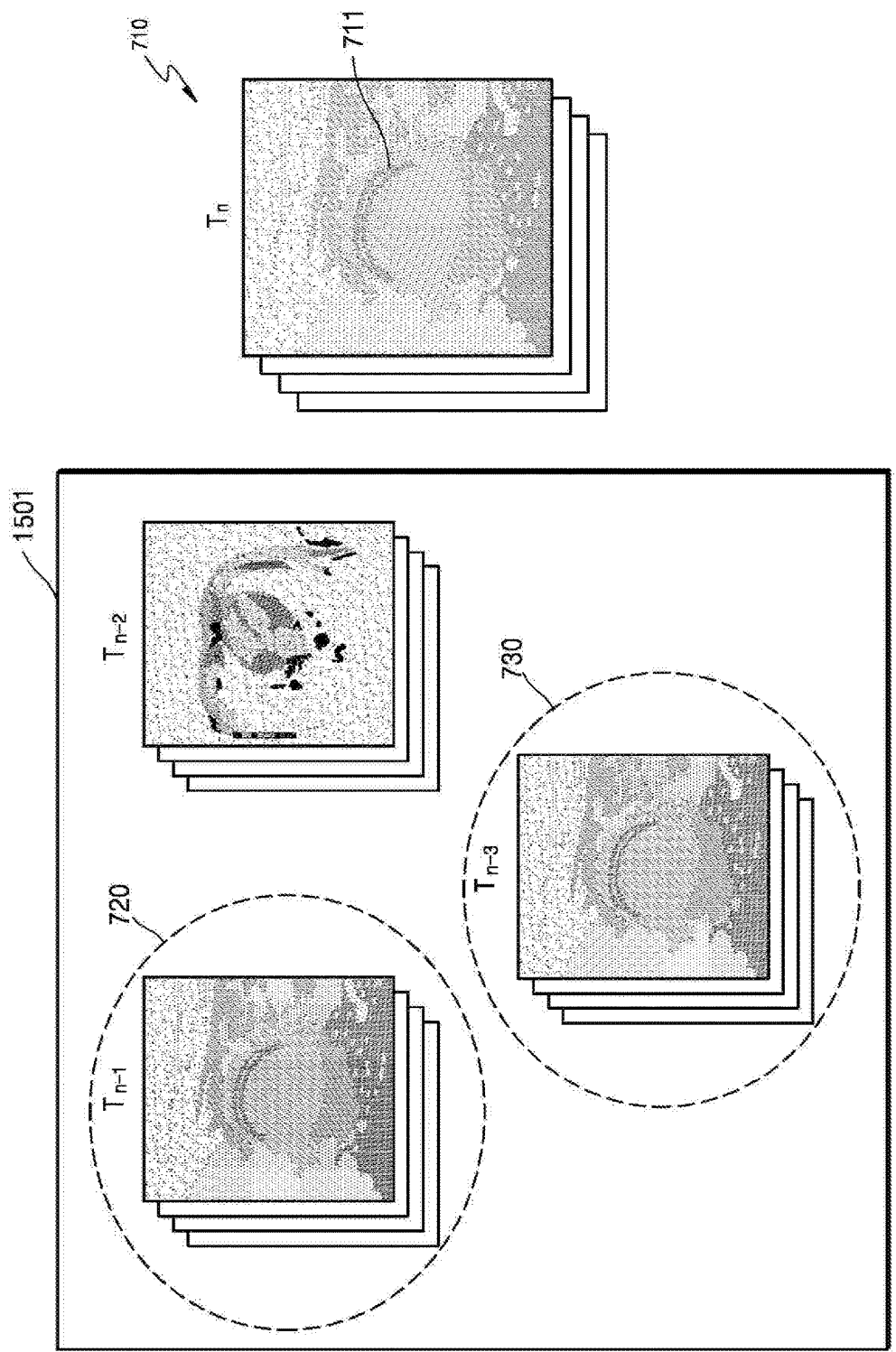
FIG. 7 illustrates an example in which a controller selects second images from among prestored images, according to an embodiment.

FIG. 7 illustrates an example in which the controller 1701 selects second images from among prestored images, according to an embodiment In detail, FIG. 7 shows an example of first images 710 generated by the image processor 1201 and images stored in the memory 1501. It is assumed herein that the first images 710 have been captured at a time point $T_n$ and the images stored in the memory 1501 have been captured at time points $T_{n-1}$, $T_{n-2}$, and $T_{n-3}$ that are earlier than the time point $T_n$.

The image processor 1201 may generate at least one first image at current time point $T_n$. In other words, the user may capture one or more first images showing an ROI 711 by using the ultrasound diagnosis systems 1000, 1001, and 1002 or the display apparatus 101.

The controller 1701 may identify the ROI 711 shown in the first images 710 and select and read captured images 720 and 720 of the same region as the ROI 711 from among images stored in the memory 1501. In this case, the images 720 and 730 may be captured respectively at different earlier time points $T_{n-1}$ and $T_{n-3}$. In other words, to observe a change in the ROI 711, the user may continue capturing images showing the ROI 711 from a specific time point in the past. For example, the user may use the ultrasound diagnosis systems 1000, 1001, and 1002 or the display apparatus 101 to capture the images 730 at the earlier time point $T_{n-3}$, the images 720 at the earlier time point $T_{n-1}$, and the images 710 at the current time point $T_n$. Furthermore, the user may capture images of a region other than the ROI 711 at the earlier time point $T_{n-2}$.

Images captured at the earlier time points $T_{n-1}$, $T_{n-2}$, and $T_{n-3}$ are stored in the memory 1501, and the controller 1701 may select and read images showing the ROI 711 from among the images stored in the memory 1501. For example, the controller 1701 may extract a shape of the ROI 711 from the first images 710 and select and read the images 720 and 730 respectively including a shape corresponding to the extracted shape.

Figure 8:
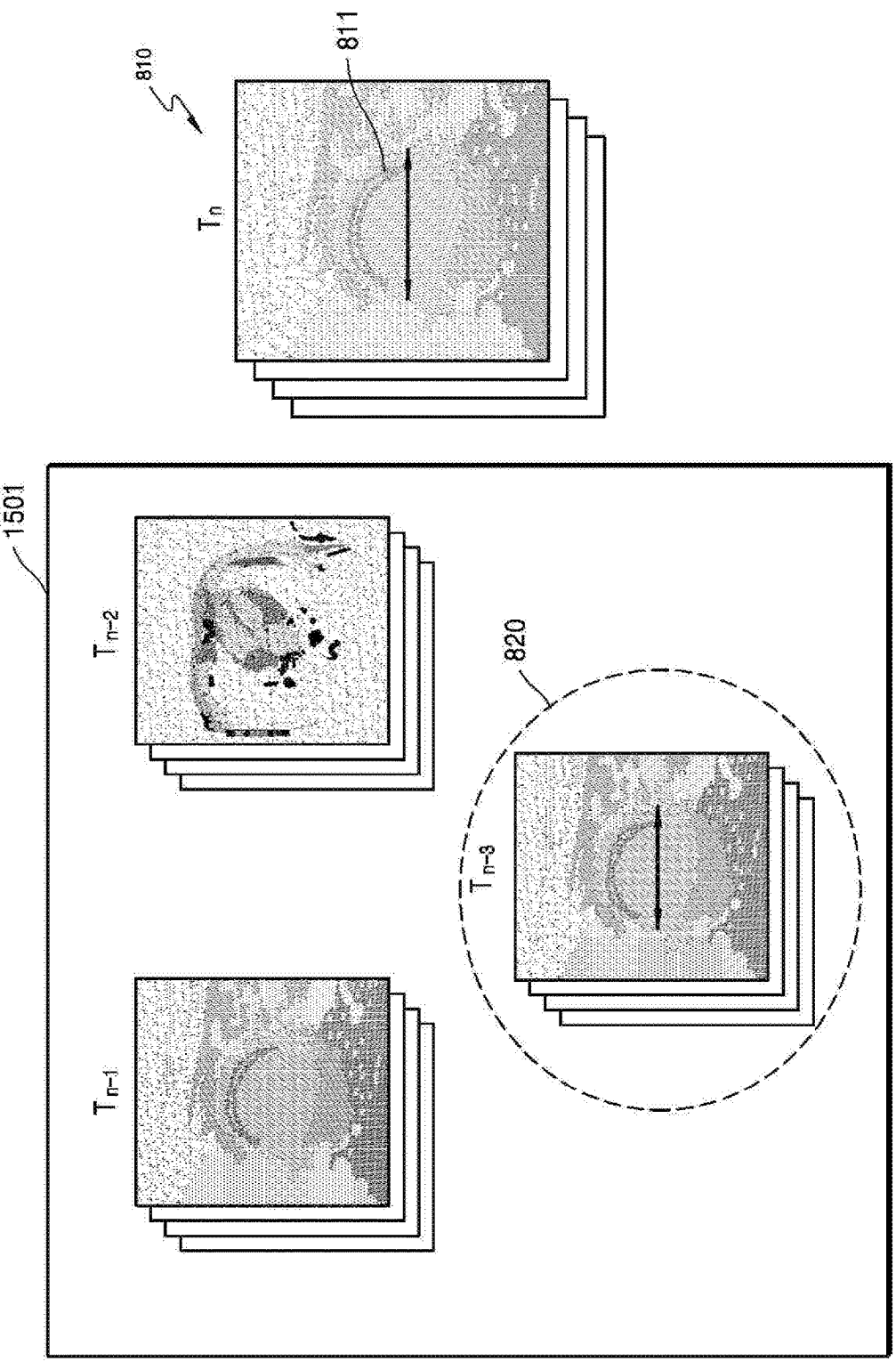
FIG. 8 illustrates another example in which a controller selects second images from among prestored images, according to an embodiment.

FIG. 8 illustrates another example in which the controller 1701 selects second images from among prestored images, according to an embodiment.

In detail, FIG. 8 shows an example of first images 810 generated by the image processor 1201 and images stored in the memory 1501. It is assumed herein that the first images 810 have been captured at a time point $T_n$ and the images stored in the memory 1501 have been captured at time points $T_{n-1}$, $T_{n-2}$, and $T_{n-3}$ that are earlier than the time point $T_n$. As described above with reference to FIG. 7, the images captured at the earlier time points $T_{n-1}$, $T_{n-2}$, and $T_{n-3}$ may be stored in the memory 1501.

The controller 1701 may select and read images 820 on which the same parameter as a parameter measured based on at least one of the first images 810 from among the images stored in the memory 1501. In this case, a parameter means a numerical value that can be measured by the user based on an image. For example, a parameter may be a size, a volume, and a length of an object (e.g., a lesion, tissue, etc.) shown in an image.

For example, if the user measures a diameter of an ROI 811 based on one of the first images 810, the controller 1701 may select and read the images 820 on which a diameter of the ROI 811 has been measured and recorded from among the images stored in the memory 1501.

Figure 9:
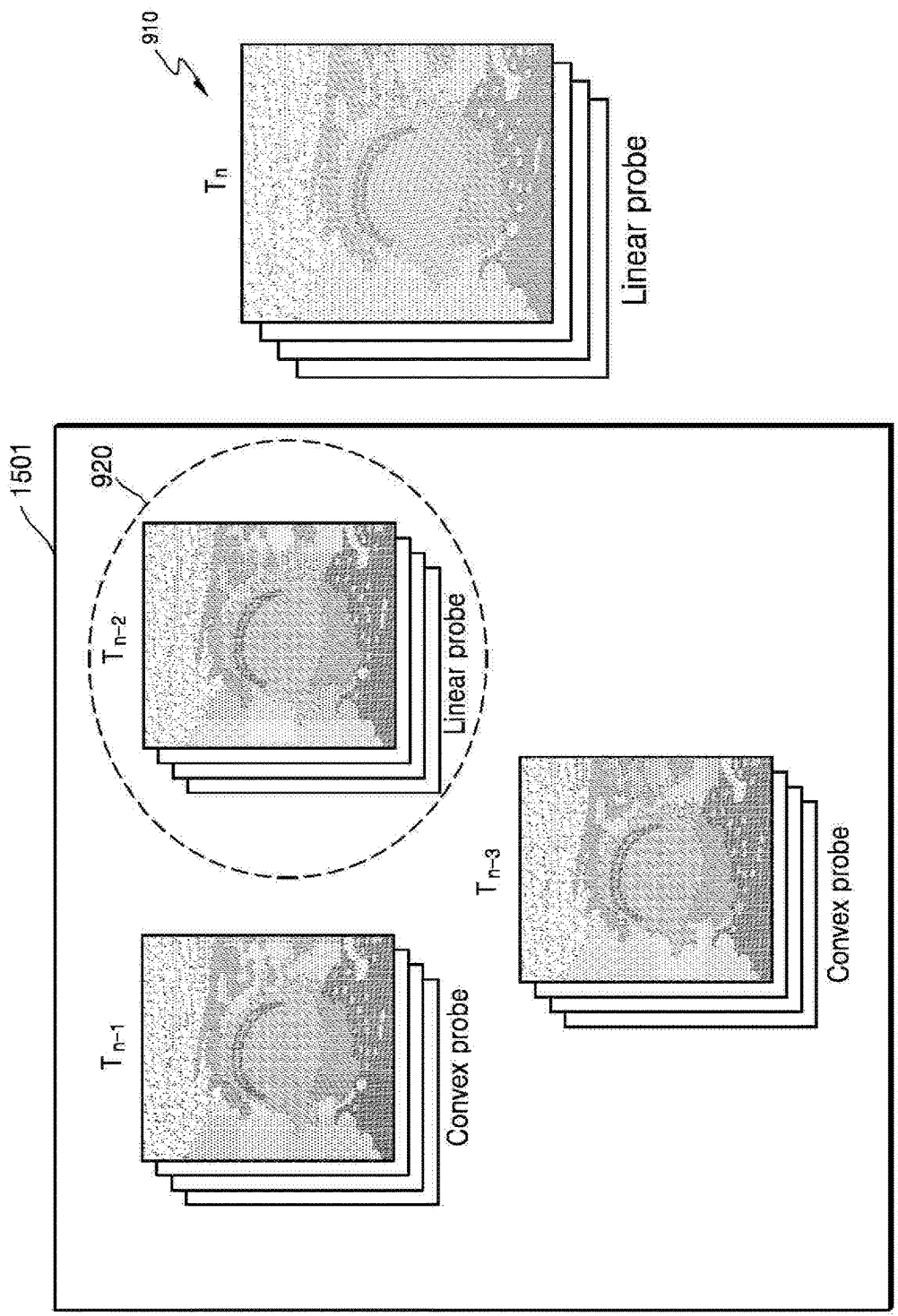
FIG. 9 illustrates another example in which a controller selects second images from among prestored images according to an embodiment.

FIG. 9 illustrates another example in which the controller 1701 selects second images from among prestored images according to an embodiment.

FIG. 9 shows an example of first images 910 generated by the image processor 1201 and images stored in the memory 1501. It is assumed herein that the first images 910 have been captured at a time point $T_n$ and the images stored in the memory 1501 have been captured at time points $T_{n-1}$, $T_{n-2}$, and $T_{n-3}$ that are earlier than the time point $T_n$. As described above with reference to FIG. 7, the images captured at the earlier time points $T_{n-1}$, $T_{n-2}$, and $T_{n-3}$ may be stored in the memory 1501.

The controller 1701 may select and read images 920 generated under the same conditions as those used to generate the first images 910 from among the images stored in the memory 1501. In this case, the conditions may be a type of the probe 20 and setting values stored in the ultrasound diagnosis systems 1000, 1001, and 1002 or the display apparatus 101. For example, the conditions may be a type of the probe 20 (a linear probe or convex probe), a TGC or LGC value of an image, a depth of the image, etc., which are used to generate the image.

For example, if the first images 910 are generated based on signals transmitted or received via a linear probe, the controller 1701 may select and read, from among the images stored in the memory 1501, the images 920 generated based on signals transmitted or received via a linear probe.

While it has been described with reference to FIGS. 7 through 9 that the controller 1701 automatically reads the second images 720, 730, 820, and 920 from the memory 1501 based on the first images 710, 810, and 910, respectively, embodiments are not limited thereto. In other words, the controller 1701 may read second images from the memory 1501 based on a user input for instructing reading of images captured at a specific time point in the past (e.g., time point $T_{n-2}$).

Referring back to FIG. 6, the display 1401 displays the first image and the second images on a screen (operation 630). In detail, the display 1401 may display the first image and the second images on a single screen in response to a control signal received from the controller 1701.

For example, the display 1401 may display thumbnail images corresponding to the second images in a region of the screen while displaying images that are most similar to the first image among the second images in a region of the screen other than the region where the thumbnail images are displayed. As another example, the display 1401 may display thumbnail images corresponding to the second images in a region of the screen while displaying an image selected based on a user input from among the second images in a region of the screen other than the region where the thumbnail images are displayed.

As another example, the display 1401 may display the second images in different regions of the screen based on time points when the second images are generated. As another example, the display 1401 may align the second images based on time points when they are generated to thereby display the aligned second images. As another example, the display 1401 may display an image that is most similar to the first image among the second images in such a manner that the most similar image is distinguished from the other ones among the second images.

Examples in which the display 1401 displays a first image and second images on a screen will be described below with reference to FIGS. 10 through 17.

Figure 10:
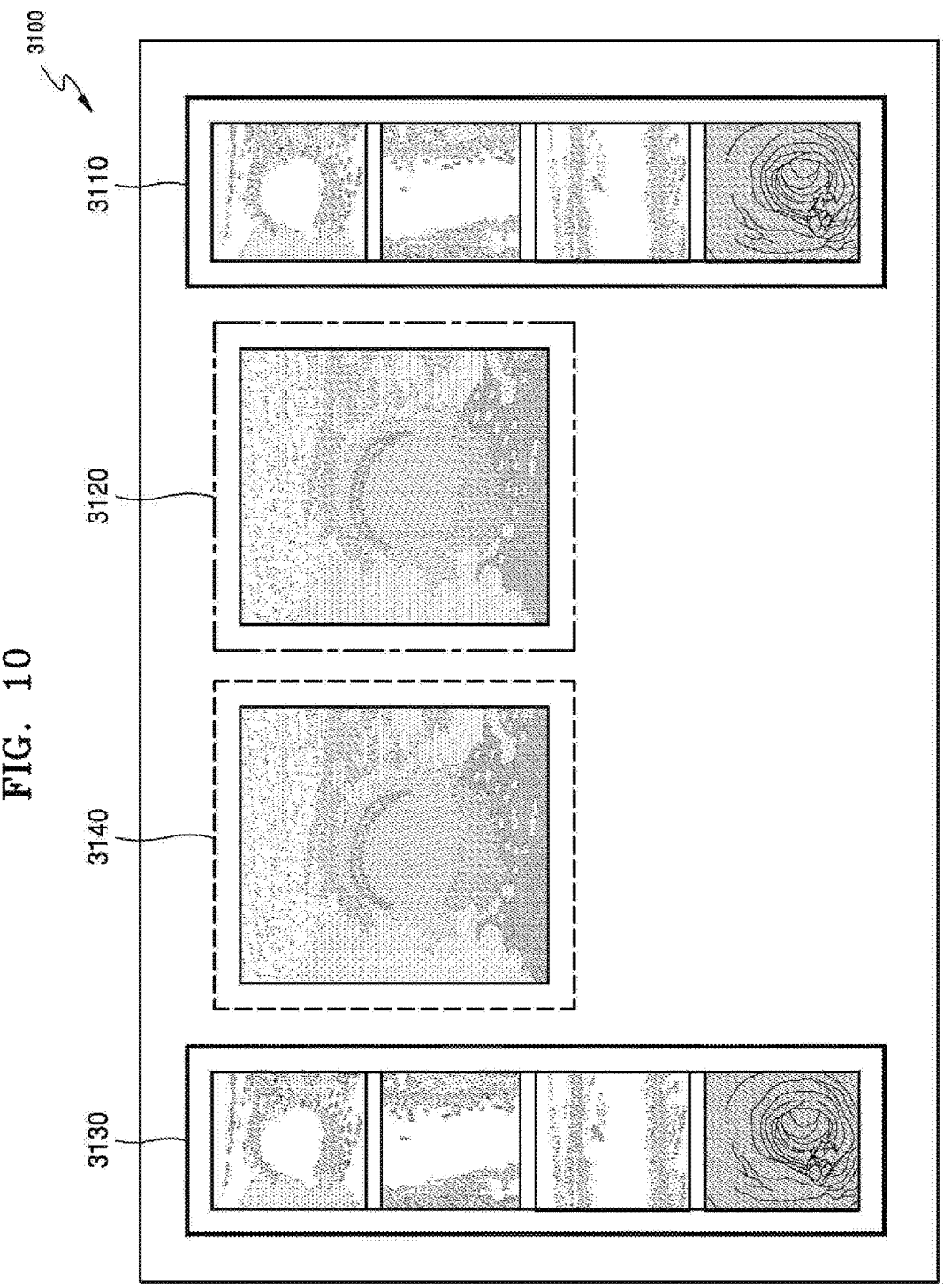
FIG. 10 illustrates an example in which first and second images are displayed on a screen, according to an embodiment.

FIG. 10 illustrates an example in which first and second images are displayed on a screen 3100, according to an embodiment FIG. 10 shows an example of the screen 3100 on which first and second images are displayed. Thumbnail images 3110 corresponding to the first images (hereinafter, referred to as 'first thumbnail images') may be displayed in a region of the screen 3100. Furthermore, thumbnail images 3130 corresponding to the second images (hereinafter, referred to as 'second thumbnail images') may be displayed in another region of the screen 3100. In this case, examples in which the controller 1701 reads the second images among images stored in the memory 1501 are as described above with reference to FIGS. 7 through 9.

A thumbnail image is a smaller version of a graphic file corresponding to an original image. Thus, thumbnail images (e.g., the first thumbnail images) hereinafter mean the same images as original images (e.g., the first images).

The controller 1701 may generate a control signal so that an image 3140 that is most similar to an image selected by the user among the second thumbnail images 3130 may be displayed in a region other than the region where the second thumbnail images 3130 are displayed.

In detail, the user may select one image from among the first thumbnail images 3110. For example, the user may select one of the first thumbnail images 3110 via the input unit 1600. If the screen 3100 is a touch screen, the user may select one image from among the first thumbnail images 3110 by performing a gesture over the screen 3100. The image selected by the user from among the first thumbnail images 3110 may be displayed as its enlarged version 3120 in a region of the screen 3100.

When the image 3120 is selected by the user, the controller 1701 may select an image that is most similar to the image 3120 from among the second thumbnail images 3130. The image selected by the controller 1701 may be displayed as its enlarged version 3140 in a region of the screen 3100.

Figure 11:
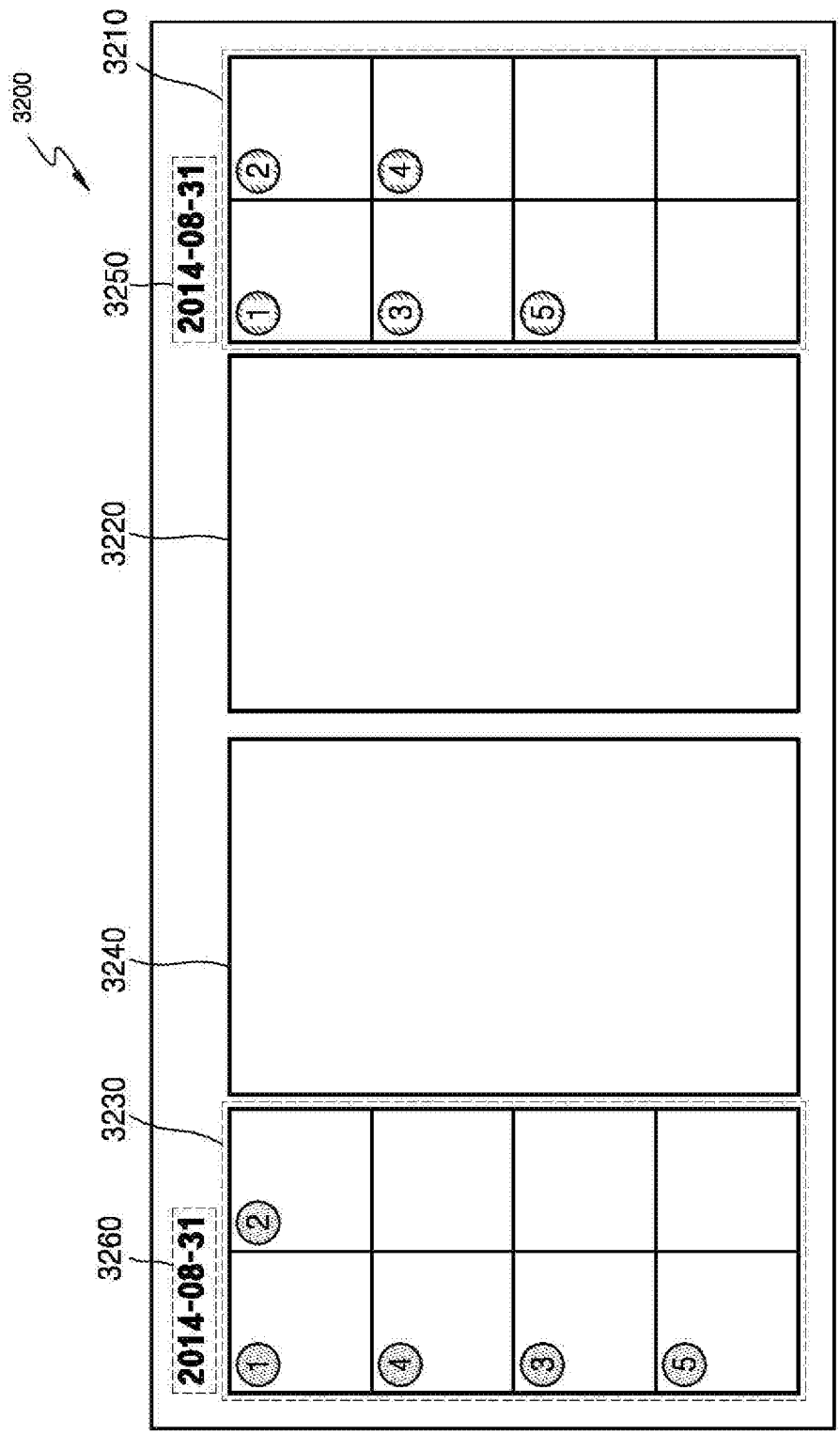
FIG. 11 illustrates another example in which first and second images are displayed on a screen, according to an embodiment.

FIG. 11 illustrates another example in which first and second images are displayed on a screen 3200, according to an embodiment.

FIG. 11 shows an example of the screen 3200 where the first and second images are displayed. In detail, first thumbnail images 3210 are displayed in a region of the screen 3200 while second thumbnail images 3230 are displayed in another region thereof. Furthermore, information 3250 about a time point when the first images are generated and information 3260 about a time point when the second images are generated may be output on the screen 3200.

In addition, results of matching the first thumbnail images 3210 to the second thumbnail images 3230 may be output on the screen 3200. In other words, information about which of the second thumbnail images 3230 is most similar to each of the first thumbnail images 3210 may be output onto the screen 3200.

The first thumbnail images 3210 (or the first images) of the same ROI may all be captured, but ROIs respectively shown in the first thumbnail images 3210 may have different shapes. For example, shapes of the ROIs respectively shown in the first thumbnail images 3210 may vary depending on a position of the probe 20 over an object or motion of the object.

The controller 1701 may compare the first thumbnail images 3210 with the second thumbnail images 3210 (or the second images), respectively, and match each of the first thumbnail images to its most similar one among the second thumbnail images 3210 based on a result of the comparison. The controller 1701 may then output matching results on the screen 3200. FIG. 11 shows an example in which the results of matching the first thumbnail images 3210 to the second thumbnail images 3230 are indicated by the same numbers.

An example in which the controller 1701 respectively matches the first thumbnail images 3210 to the second thumbnail images 3230 will now be described in detail with reference to FIG. 12.

Figure 12:
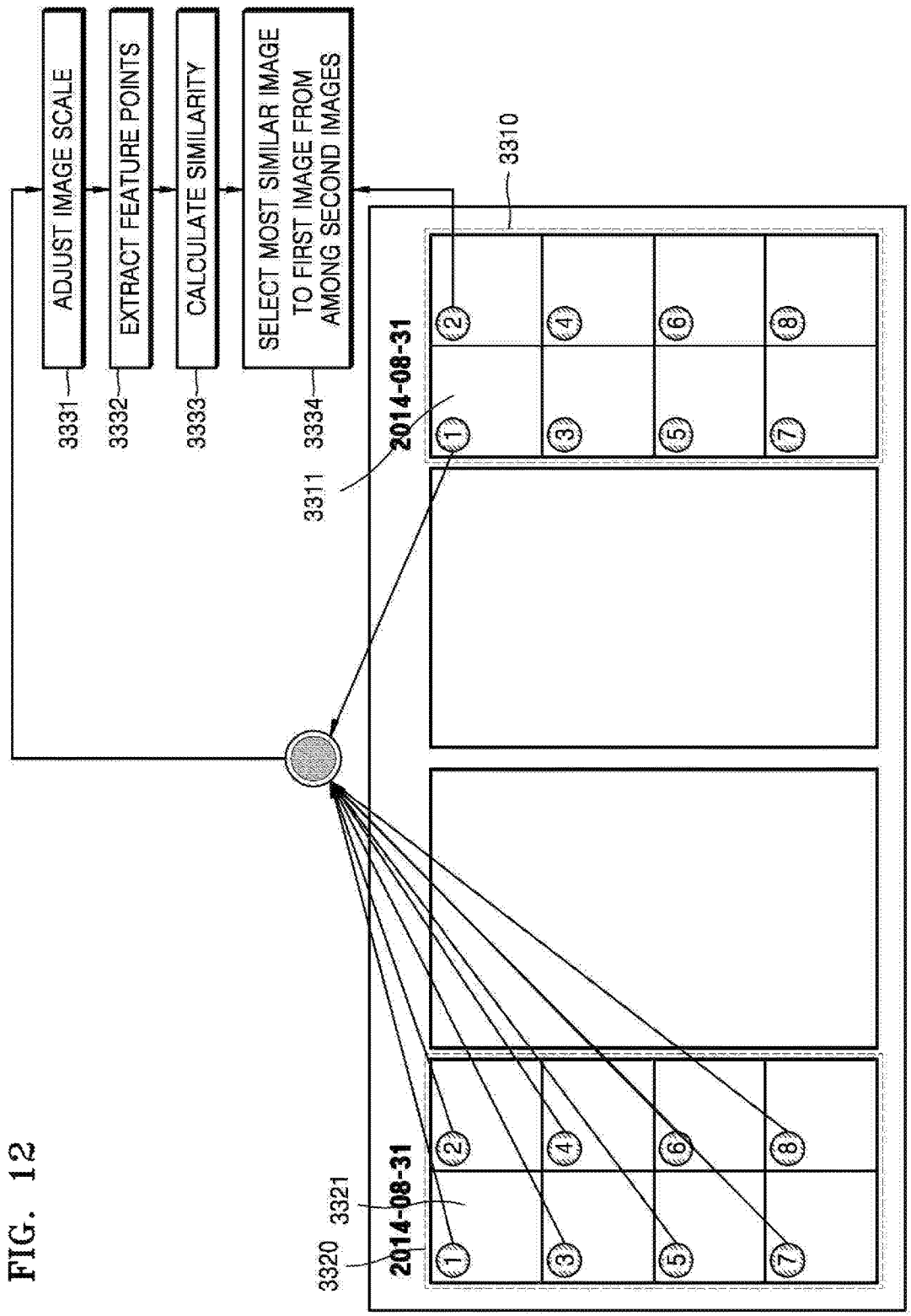
FIG. 12 illustrates an example in which a controller matches first thumbnail images to second thumbnail images according to an embodiment.

FIG. 12 illustrates an example in which the controller 1701 matches first thumbnail images 3310 to second thumbnail images 3320 according to an embodiment.

Referring to FIG. 12, the controller 1701 selects one image 3311 from among the first thumbnail images 3310. The controller 1701 also compares the image 3311 with each of the second thumbnail images 3320.

In detail, the controller 1701 may adjust a scale of the image 3311 or the second thumbnail images 3320 so that the image 3311 and the second thumbnail images 3320 have the same scale (operation 3331). For example, the controller 1701 may adjust a scale of the image 3311 or the second thumbnail images 3320 by enlarging or reducing the image 3311 or the second thumbnail images 3320 or using a depth of the image 3311 or the second thumbnail images 3320.

The controller 1701 extracts feature points from the image 3311 and the second thumbnail images 3320 according to a feature-based algorithm (operation 3332). The controller 1701 then uses the extracted feature points to calculate a similarity between the image 3311 and each of the second thumbnail images 3320 (operation 3333). In operations 3332 and 3333, the controller 1701 may extract feature points from the image 3311 and the second thumbnail images 3320 and calculate a similarity therebetween by using various algorithms. For example, the controller 1701 may perform operations 3332 and 3333 by using an algorithm such as Histogram of Oriented Gradient (HOG), Scale Invariant Feature Transform (SIFT), Haar-like features, Ferns, Local Binary Pattern (LBP), or Modified Census Transform (MCT).

The controller 1701 selects an image 3321 that is most similar to the image 3311 from among the second thumbnail images 3320 (operation 3334). Then, the display 1401 outputs information indicating that the selected image 3321 is most similar to the image 3311 on a screen. For example, the display 1401 may output the same marker (e.g., the same number) on the images 3311 and 3321 in order to indicate that the images 3311 and 3321 are most similar ones.

The controller 1701 may perform operations 3331 through 3334 on each of the other ones among the first thumbnail images 3310 in order to respectively match the first thumbnail images 3310 to the second thumbnail images 3320.

As described above with reference to FIGS. 10 through 12, second images (or second thumbnail images) include images generated at a time point in the past. However, the second images may include images generated at each of a plurality of time points in the past. Examples in which second images generated at a plurality of earlier time points are displayed on a screen will now be described with reference to FIGS. 13 and 14.

Figure 13:
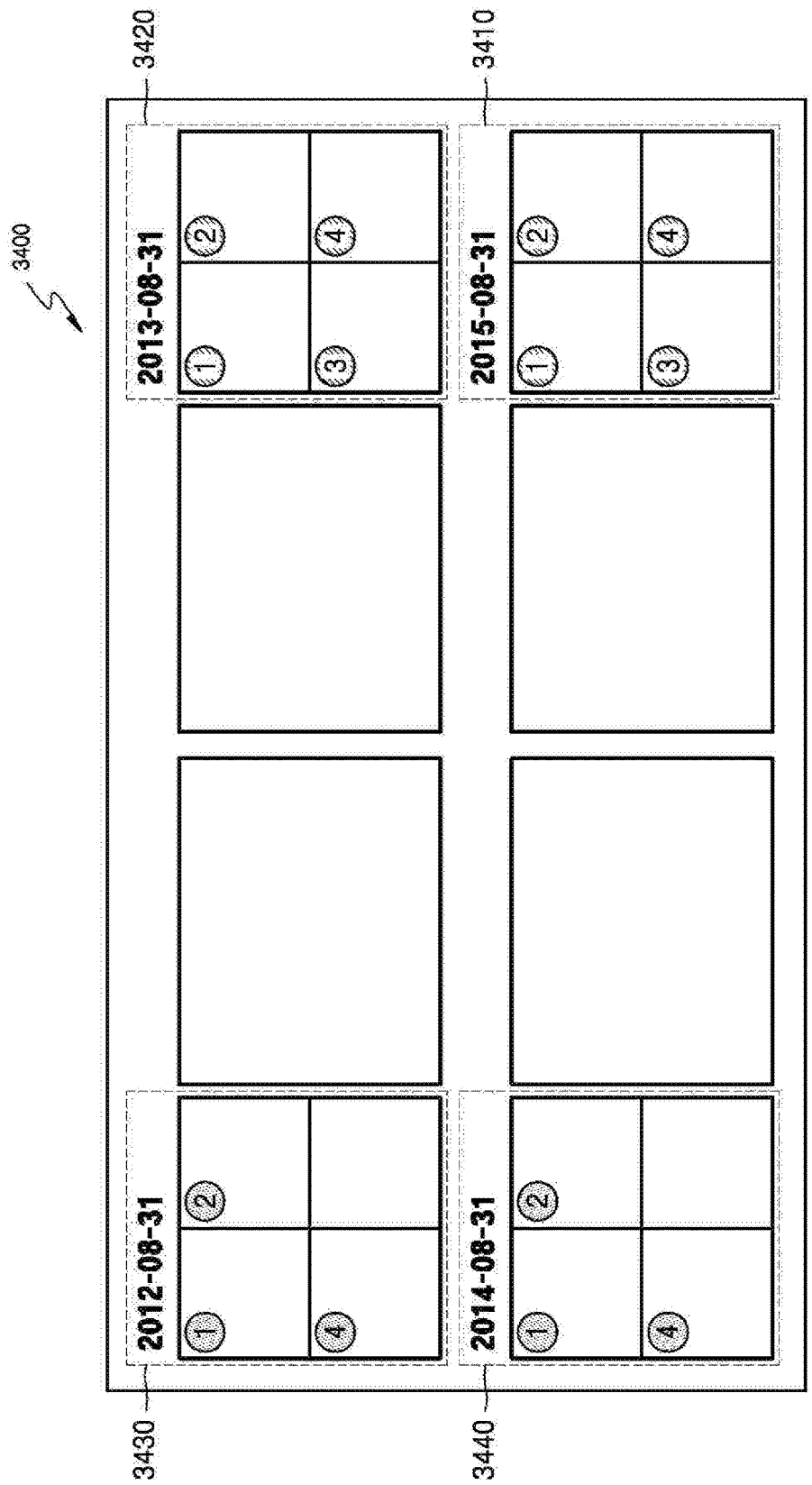
FIG. 13 illustrates another example in which first and second images are displayed on a screen, according to an embodiment.

FIG. 13 illustrates another example in which first and second images are displayed on a screen 3400, according to an embodiment FIG. 13 shows an example in which a plurality of thumbnail images 3410, 3420, 3430, and 3440 are displayed on the screen 3400. For example, first thumbnail images 3410 may be generated at a current time point, and second thumbnail images 3420, 3430, and 3440 may respectively be generated at a plurality of earlier time points.

As described above with reference to FIGS. 7 through 9, the controller 1701 may read images (e.g., the second thumbnail images 3420, 3430, and 3440) related to the first thumbnail images 3410 among a plurality of images stored in the memory 1501. In this case, when the related images are generated at different time points, the display 1401 may display the related images respectively in different regions of the screen 3400 based on the time points when they are generated.

Furthermore, as described with reference to FIGS. 7 through 9, the controller 1701 may select images selected based on a user input from among images stored in the memory 1501. In this case, referring to FIG. 13, the display 1401 may display images (e.g., the second thumbnail images 3420, 3430, and 3440) generated at time points selected by the user.

In addition, as described above with reference to FIGS. 11 and 12, the controller 1701 may compare the first thumbnail images 3410 with the second thumbnail images 3420, 3430, and 3440, respectively, and match each of the first thumbnail images 410 to its most similar ones among the second thumbnail images 3420, 3430, and 3440 based on results of the comparison. The controller 1701 may then output matching results on the screen 3400. However, if the second thumbnail images 3420, 3430, or 3440 include an image that is not similar to any one of the first thumbnail images 3410, a matching result may not be output on the screen 3400.

For example, if an image similar to image ③ among the first thumbnail images 3410 is not included in the second thumbnail images 3430 and 3440 respectively captured on Aug. 31, 2012 and Aug. 31, 2014, a matching result may not be output on the screen 3400. For example, as described above with reference to FIG. 12, if the second thumbnail images 3430 and 3440 do not include any image whose similarity with image ③ among the first thumbnail images 3410 is greater than a predetermined value, a matching result may not be output on the screen 3400.

Figure 14:
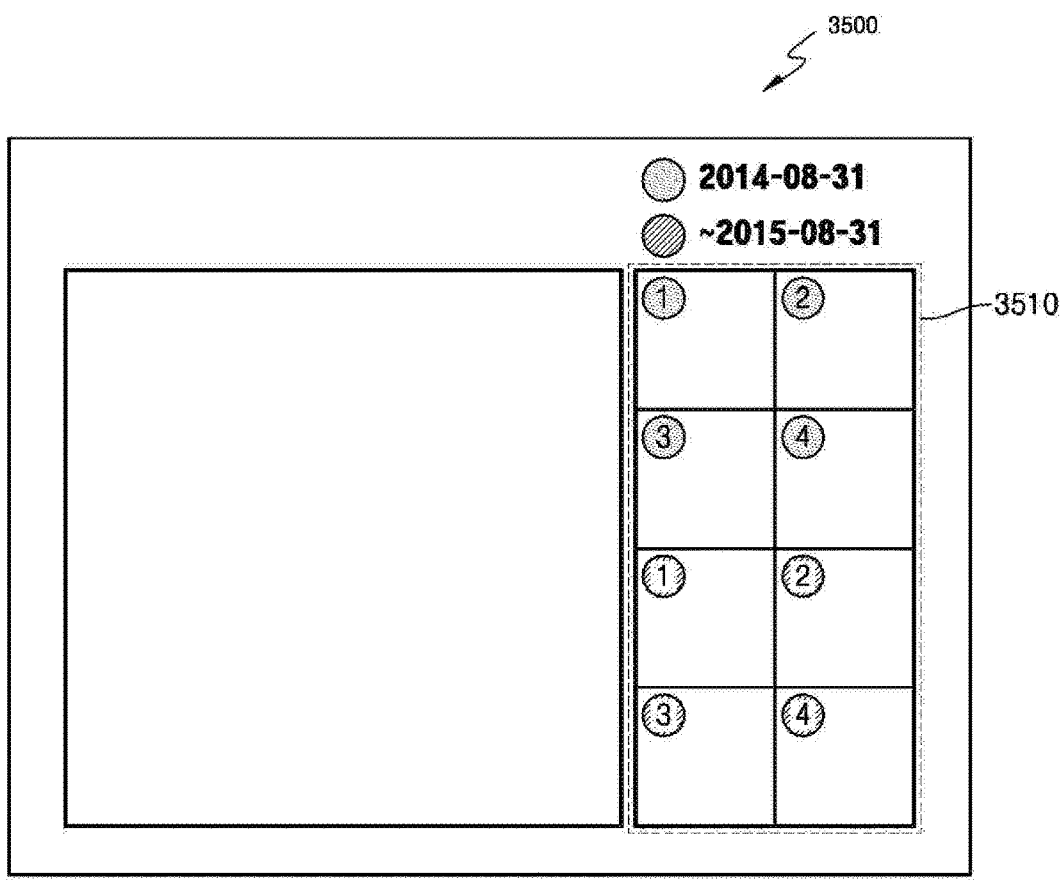
FIG. 14 illustrates another example in which first and second images are displayed on a screen, according to an embodiment.

FIG. 14 illustrates another example in which first and second images are displayed on a screen 3500, according to an embodiment.

FIG. 14 shows an example in which a plurality of thumbnail images 3510 are displayed on the screen 3500. For example, the plurality of thumbnail images 3510 may include first and second thumbnail images, and may be aligned based on time points when the plurality of thumbnails 3510 are generated and displayed in a region of the screen 3500.

For example, if the first thumbnail images are captured on Aug. 31, 2015 and the second thumbnail images are captured on Aug. 31, 2014, the plurality of thumbnails 3510 may be displayed on the screen 3500 in an order from the first thumbnail images to the second thumbnail images or from the second thumbnail images to the first thumbnail images.

Although not shown in FIG. 14, the second thumbnail images may include images captured at a plurality of time points. In this case, thumbnail images may be aligned according to an order of time points when the first thumbnail images are captured and when the second thumbnail images are captured and displayed on the screen 3500.

As described with reference to FIGS. 11 through 14, results of matching first images (or first thumbnail images) to second images (or second thumbnail images) may be output on a screen. In addition, when the user selects one image from among the images (e.g., the first and second images), output on the screen, the display 1401 may display an image that is most similar to the selected image in such a manner that the most similar image is distinguished from the other ones. Examples in which the display 1401 displays an image that is most similar to an image selected by the user in such a manner that the most similar image is distinguished from the other ones will now be described in detail with reference to FIGS. 15 through 17.

Figure 15:
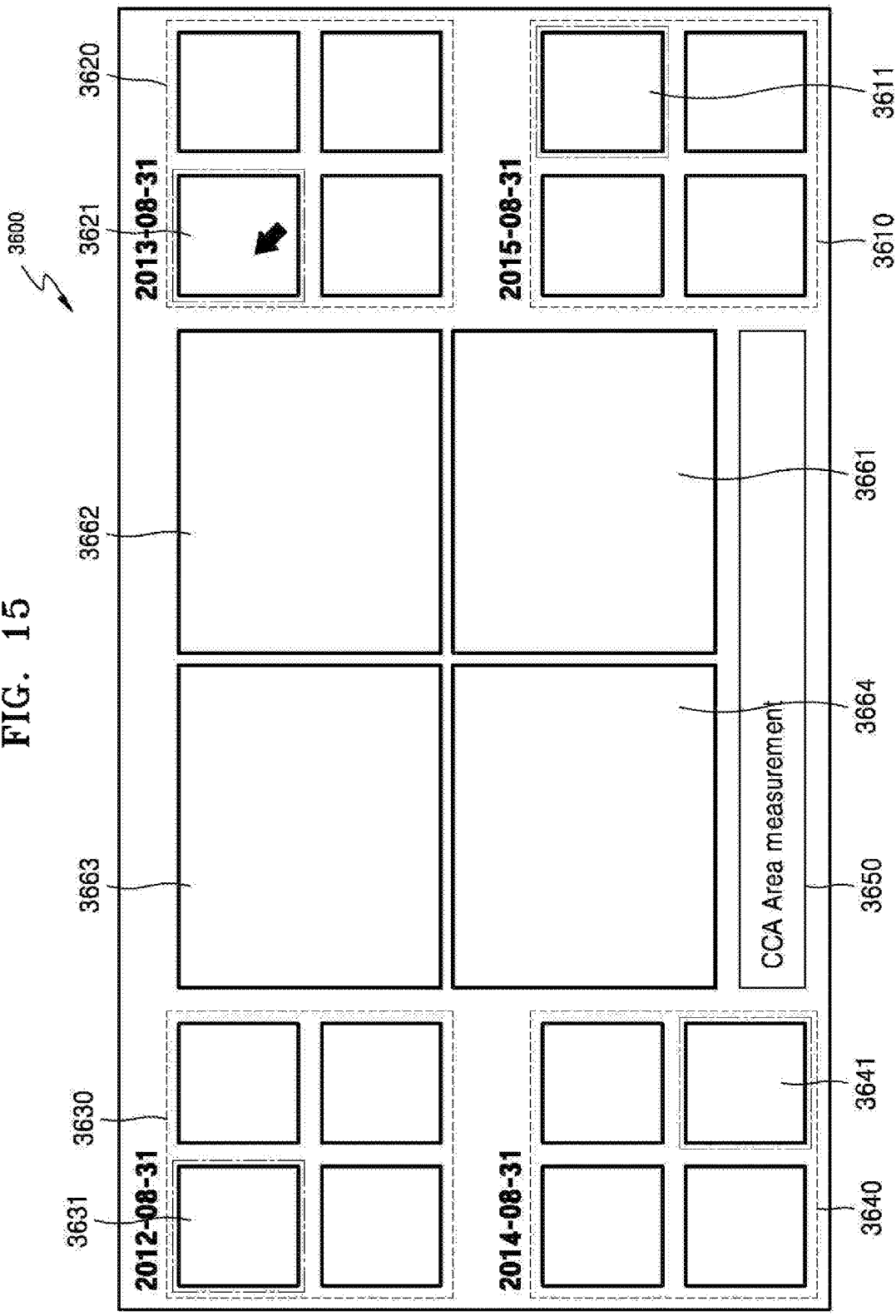
FIG. 15 illustrates another example in which first and second images are displayed on a screen, according to an embodiment.

FIG. 15 illustrates another example in which first and second images are displayed on a screen 3600, according to an embodiment;

FIG. 15 shows an example of the screen 3600 on which a plurality of thumbnail images 3610, 3620, 3630, and 3640 are displayed. It is assumed herein that thumbnail images

3610 among the plurality of thumbnail images 3610, 3620, 3630, and 3640 are first thumbnail images.

The user may select one thumbnail image 3621 from among the plurality of thumbnail images 3610, 3620, 3630, and 3640. In this case, the thumbnail image 3621 selected by the user may be a first or second thumbnail image. For example, the user may select the thumbnail image 3621 from among the plurality of thumbnail images 3610, 3620, 3630, and 3640 via the input unit 1600. If the screen 3600 is a touch screen, the user may select the thumbnail image 3621 from among the plurality of thumbnail images 3610, 3620, 3630, and 3640 by performing a gesture over the screen 3600. The thumbnail image 3621 selected by the user may be displayed as its enlarged version 3662 in a region of the screen 3600.

When the user selects the thumbnail image 3621, the controller 1701 selects images 3611, 3631, and 3641 that are most similar to the thumbnail image 3621 respectively from among the thumbnail images 3610, 3630, and 3640. Then, the display 1401 displays the selected images 3611, 3631, and 3641 on the screen 3600 so that they are distinguished from the other images. Furthermore, the display 1401 may display the selected images 3611, 3631, and 3641 respectively as their enlarged versions 3661, 3663, and 3664 in a region of the screen 3600.

If there is a history of measurement of a parameter based on the thumbnail image 3621 selected by the user, the display 1401 may output information 3650 about the type of the measured parameter on a region of the screen 3600.

Figure 16:
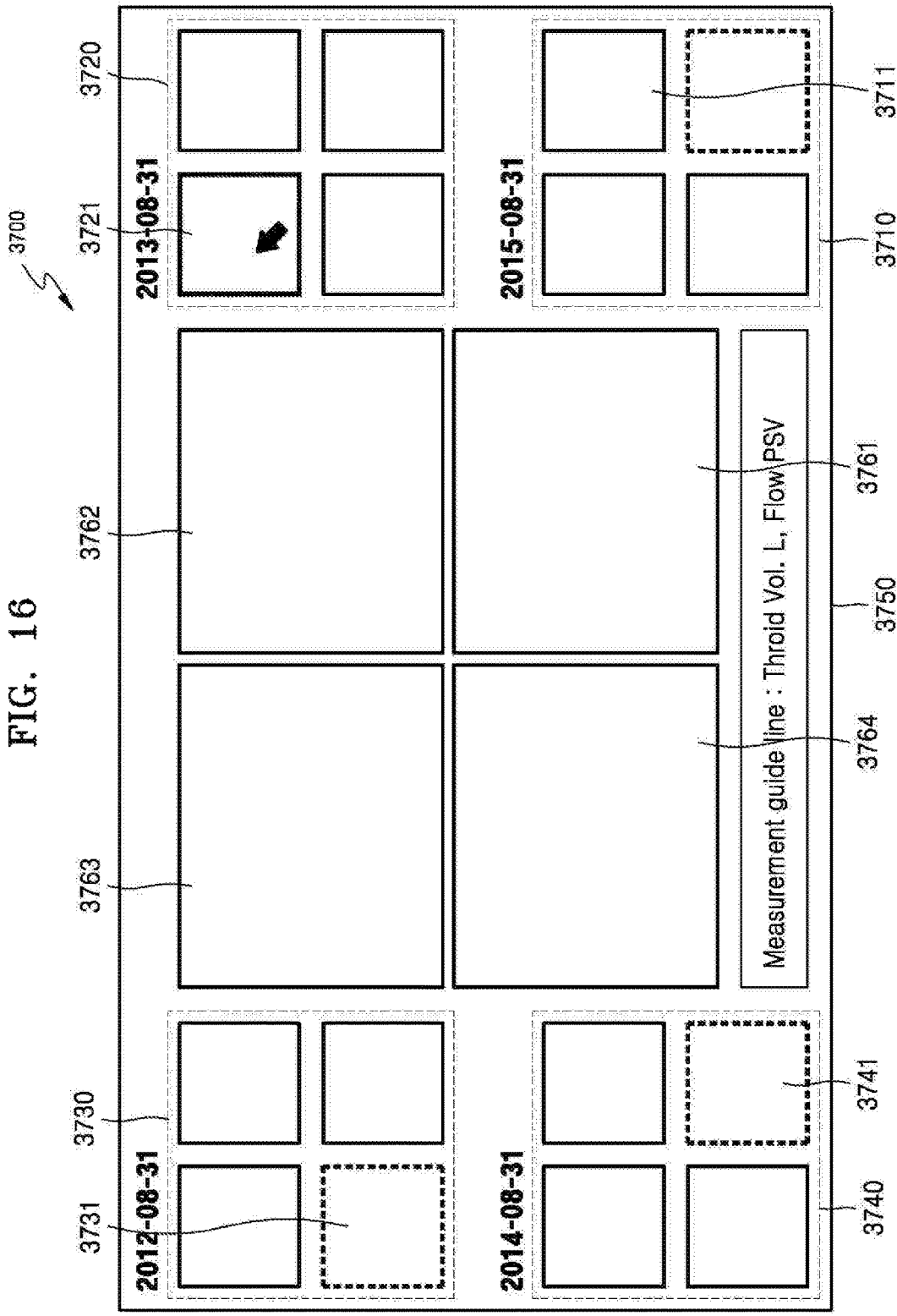
FIG. 16 illustrates another example in which first and second images are displayed on a screen, according to an embodiment.

FIG. 16 illustrates another example in which first and second images are displayed on a screen 3700, according to an embodiment;

FIG. 16 shows an example of the screen 3700 on which a plurality of thumbnail images 3710, 3720, 3730, and 3740 are displayed. It is assumed herein that thumbnail images 3710 among the plurality of thumbnail images 3710, 3720, 3730, and 3740 are first thumbnail images.

The user may select one thumbnail image 3721 from among the plurality of thumbnail images 3710, 3720, 3730, and 3740. In this case, the thumbnail image 3721 selected by the user may be a first or second thumbnail image.

When the user selects the thumbnail image 3721, the controller 1701 selects images 3711, 3731, and 3741, on which the same parameter as a parameter measured based on the thumbnail image 3721 is measured, from among the thumbnail images 3710, 3730, and 3740. Then, the display 1401 displays the selected images 3711, 3731, and 3741 on the screen 3700 so that they are distinguished from the other images. Furthermore, the display 1401 may display the selected images 3711, 3731, and 3741 respectively as their enlarged versions 3761, 3763, and 3764 in a region of the screen 3700. Furthermore, the display 1401 may output information 3750 about the type of a measured parameter on a region of the screen 3700.

Although not shown in FIG. 16, when the user selects the thumbnail image 3721, the controller 1701 may select the images 3711, 3731, and 3741 that are generated under the same conditions as those used to generate the thumbnail image 3721 respectively from among the thumbnail images 3710, 3730, and 3740. Then, the display 1401 may display the selected images 3711, 3731, and 3741 on the screen 3700 so that they are distinguished from the other images.

Figure 17:
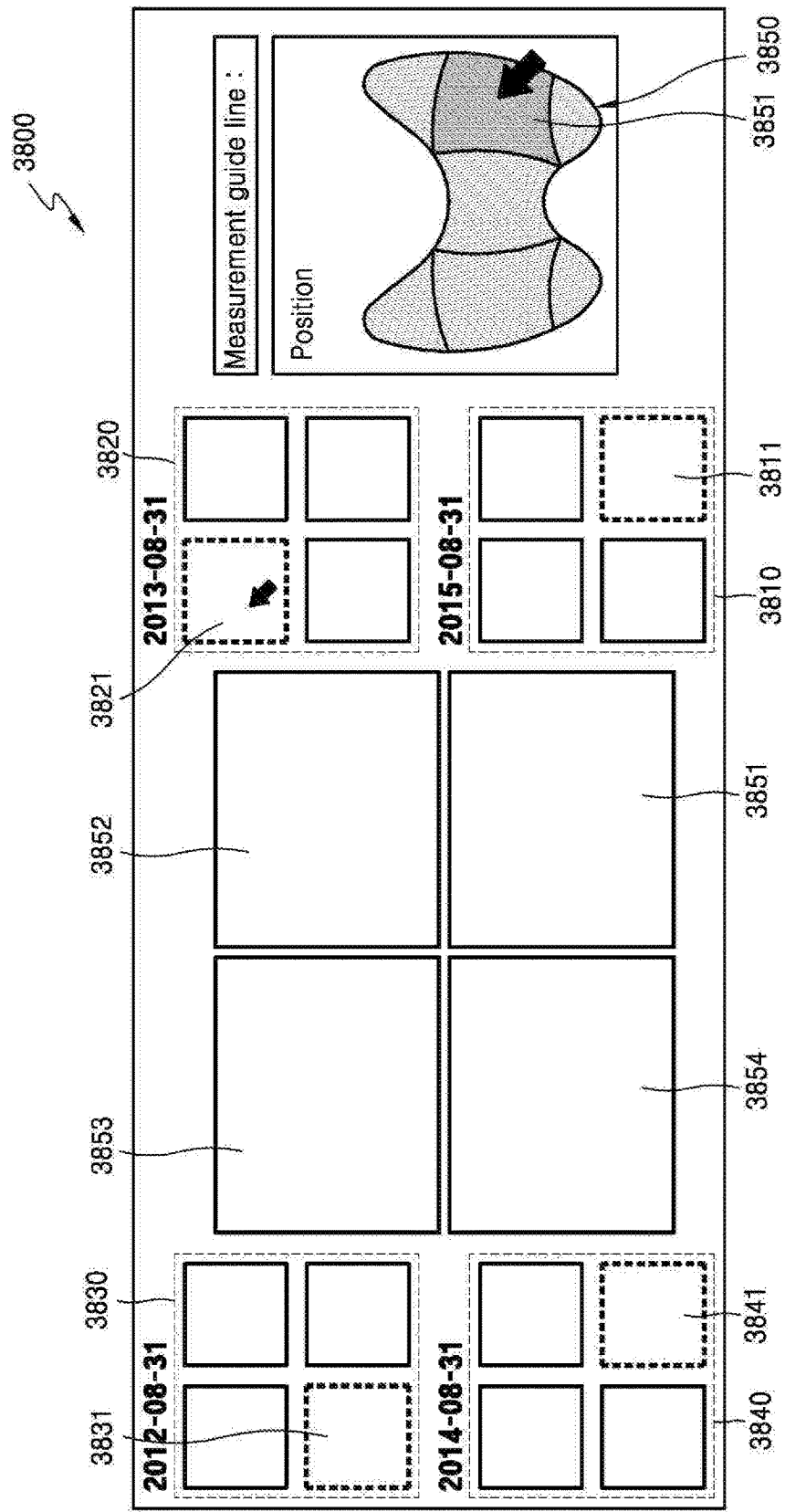
FIG. 17 illustrates another example in which first and second images are displayed on a screen, according to an embodiment.

FIG. 17 illustrates another example in which first and second images are displayed on a screen 3800, according to an embodiment.

FIG. 17 shows an example of the screen 3800 on which a plurality of thumbnail images 3810, 3820, 3830, and 3840 are displayed. It is assumed herein that thumbnail images 3810 among the plurality of thumbnail images 3810, 3820, 3830, and 3840 are first thumbnail images.

In addition, an object 3850 representing an ROI as well as the thumbnail images 3810, 3820, 3830, and 3840 are displayed on the screen 3800. In this case, the object 3850 may be a body marker representing the ROI.

When the user selects a portion 3851 of the object 3850, the controller 1701 selects images 3811, 3821, 3831, and 3841 showing the selected portion 3851 from among the thumbnail images 3810, 3820, 3830, and 3840. The display 1401 displays the selected images 3811, 3821, 3831, and 3841 on the screen 3800 so that they are distinguished from the other images. Furthermore, the display 1401 may display the selected images 3811, 3821, 3831, and 3841 respectively as enlarged versions 3851, 3852, 3853, and 3854 in a region of the screen 3800.

As described above with reference to FIGS. 6 through 17, the ultrasound diagnosis systems 1000, 1001, and 1002 or the display apparatus 1001 may display second images that are most similar to a first image on a screen. Furthermore, the ultrasound diagnosis systems 1000, 1001, and 1002 or the display apparatus 101 may display on the screen second images used to measure the same parameter as a parameter measured based on the first image. Furthermore, the ultrasound diagnosis systems 1000, 1001, and 1002 or the display apparatus 101 may display on the screen the second images generated under the same conditions as those used to generate the first image In addition, the ultrasound diagnosis systems 1000, 1001, and 1002 may output on a screen parameter values measured based on images (i.e., first and second images). In other words, if there is a history of measurement of a specific parameter on the same ROI from a time point in the past, the ultrasound diagnosis systems 1000, 1001, and 1002 or the display apparatus 101 may output measured values of the parameter on the screen. Examples in which measured values of a parameter are output onto a screen will now be described with reference to FIGS. 18A through 18D.

FIGS. 18A through 18D illustrate examples in which measured values of a parameter are output on a screen, according to an embodiment.

FIGS. 18A through 18D show examples in which values of a parameter are aligned based on an order of time points of measurement and output on a screen. Referring to FIGS. 18A and 18B, a graph showing a time point when a parameter is measured on an x-axis and a value of the parameter on a y-axis may be output on the screen. Furthermore, referring to FIG. 18C, images on which the parameter is measured may be aligned in order of time and output onto the screen. Furthermore, referring to FIG. 18D, measured values of the parameter may be output on the screen in a table form.

A mode in which measured values of a parameter are output is not limited to the examples shown in FIGS. 18A through 18D and may be changed in various ways depending on user settings.

As described above, the user may identify how an ROI changes over time based on images displayed by the display apparatus 101. Furthermore, the display apparatus 101 may automatically select an image similar to a currently captured image from among prestored images and display the automatically selected image, so the amount of time that it takes for the user to diagnose an object based on the image may be shortened.

The above methods according to the embodiments can be recorded in programs that can be executed on a computer and be implemented through general purpose digital computers which can run the programs using a non-transitory computer-readable recording medium. Data structures described in the above methods can also be recorded on a non-transitory computer-readable medium in a variety of ways, with examples of the medium including recording media, such as magnetic storage media (e.g., ROM, RAM, USB, floppy disks, hard disks, etc.) and optical recording media (e.g., CD-ROMs or DVDs).

While one or more embodiments have been described with reference to the figures, it will be understood by those of ordinary skill in the art that various changes in form and details may be made therein without departing from the spirit and scope of the inventive concept as defined by the following claims. Thus, it should be understood that the embodiments described therein should be considered in a descriptive sense only and not for purposes of limitation. The scope of the present inventive concept is defined not by the detailed description thereof but by the appended claims, and all differences within the scope of the appended claims and their equivalents will be construed as being included in the present inventive concept.

What is claimed is:

1. A method of displaying a medical image, the method comprising:
    generating, by a processor, images of a plurality of objects by using echo signals corresponding to ultrasound signals transmitted toward targets of the plurality of objects, respectively, and storing the images of the plurality of objects in a memory;
    generating first images showing a region of interest (ROI) of a target of a subject at a first time point by using echo signals corresponding to ultrasound signals transmitted toward the target of the subject;
    selecting second images that show the ROI of the target of the subject from the stored images of the plurality of objects, wherein the second images are generated at at least one second time point earlier than the first time point and stored in the memory; and
    displaying a body marker representing the ROI and the first images together with the second images on a screen, wherein the screen is partitioned into a plurality of different regions, the displaying comprising displaying a plurality of first thumbnail images corresponding to the first images and a plurality of second thumbnail images corresponding to the second images, in the plurality of different regions into which the screen is partitioned based on the first time point and the at least one second time point when the first images and the second images are respectively generated,
    wherein the method further comprises:
        comparing each of the plurality of first thumbnail images with each of the plurality of second thumbnail images, and matching each of the plurality of first thumbnail images with its most similar second thumbnail image among the plurality of second thumbnail images, based on the comparing,
        displaying results of the matching indicating each of the plurality of first thumbnail images and its most similar second thumbnail image among the plurality of second thumbnail images, wherein the results of the matching of each of the plurality of first thumbnail images to its most similar second thumbnail image are indicated by displaying a same thumbnail marker on each of the plurality of first thumbnail images and its most similar second thumbnail image, respectively,
        receiving a selection of a portion of the body marker, selecting images showing the portion of the body marker from the plurality of first thumbnail images and the plurality of second thumbnail images, based on the results of the matching that are displayed, and displaying the images showing the portion of the body marker.

2. The method of claim 1, wherein the displaying the images showing the portion of the body marker comprises:
    displaying the images showing the portion of the body marker in an area of the screen other than an area where the plurality of first thumbnail images and the plurality of second thumbnail images are displayed.

3. The method of claim 1, wherein the portion of the body marker is selected based on a user input, and
    the displaying the images showing the portion of the body marker comprises displaying the images showing the portion of the body marker in an area of the screen other than an area where the plurality of first thumbnail images and the plurality of second thumbnail images are displayed.

4. The method of claim 1, wherein the at least one second time point is a time point selected based on a user input from among second time points at which the second images are respectively generated.

5. The method of claim 1, wherein the displaying the plurality of first thumbnail images and the plurality of second thumbnail images comprises:
    aligning the plurality of second thumbnail images based on second time points when the second images are respectively generated, and
    displaying the aligned plurality of second thumbnail images,
    wherein the at least one second time point is one of the second time points.

6. The method of claim 1, wherein the displaying the images showing the portion of the body marker comprises:
    displaying at least one of the images showing the portion of the body marker to be distinguished from the plurality of first thumbnail images and the plurality of second thumbnail images.

7. The method of claim 1, further comprising measuring a parameter of the ROI based on at least one of the first images,
    wherein the selecting the second images comprises selecting, from the stored images of the plurality of objects, images on which the parameter is measured, as the second images.

8. The method of claim 1, wherein the first images are generated under a first condition,
    wherein the selecting the second images comprises selecting, from the stored images of the plurality of objects, images generated under the first condition, as the second images.

9. A non-transitory computer-readable recording medium having recorded thereon a program which, when executed by a computer, causes the computer to execute the method of claim 1.

10. An apparatus for displaying a medical image, the apparatus comprising:
    an image processor configured to generate images of a plurality of objects by using echo signals corresponding to ultrasound signals transmitted toward targets of the plurality of objects, respectively, and to generate first images showing a region of interest (ROI) of a target of a subject at a first time point by using echo signals corresponding to ultrasound signals transmitted toward the target of the subject;

a memory configured to store the images of the plurality of objects;

a controller configured to select second images that show the ROI of the target of the subject, from the stored images of the plurality of objects, wherein the second images are generated at at least one second time point earlier than the first time point and stored in the memory; and a display configured to display a body marker representing the ROI and the first images together with the second images on a screen, wherein the screen is partitioned into a plurality of different regions, based on a control signal generated by the controller, wherein the controller is further configured to generate the control signal to:

control the display to display a plurality of first thumbnail images corresponding to the first images and a plurality of second thumbnail images corresponding to the second images, in the plurality of different regions into which the screen is partitioned, based on the first time point and the at least one second time point when the first images and the second images are respectively generated, compare each of the plurality of first thumbnail images with each of the plurality of second thumbnail images, and match each of the plurality of first thumbnail images with its most similar second thumbnail image among the plurality of second thumbnail images, based on the comparing, control the display to display results of the matching indicating each of the plurality of first thumbnail images and its most similar second thumbnail image among the plurality of second thumbnail images, wherein the results of the matching of each of the plurality of first thumbnail images to its most similar second thumbnail image are indicated by displaying a same thumbnail marker on each of the plurality of first thumbnail images and its most similar second thumbnail image, respectively, receive a selection of a portion of the body marker, select images showing the portion of the body marker from the plurality of first thumbnail images and the plurality of second thumbnail images, based on the results of the matching that are displayed, and control the display to display the images showing the portion of the body marker.

11. The apparatus of claim 10, wherein the controller is further configured to generate the control signal so that the images showing the portion of the body marker are displayed in an area of the screen other than an area where the plurality of first thumbnail images and the plurality of second thumbnail images are displayed.

12. The apparatus of claim 10, wherein the portion of the body marker is selected based on a user input, and the controller is further configured to generate the control signal so that the images showing the portion of the body marker are displayed in an area of the screen other than an area where the plurality of first thumbnail images and the plurality of second thumbnail images are displayed.

13. The apparatus of claim 10, wherein the at least one second time point is a time point selected based on a user input from among second time points at which the second images are respectively generated.

14. The apparatus of claim 10, wherein the controller is further configured to generate the control signal so that the plurality of second thumbnail images are aligned based on second time points when the second images are respectively generated, and to control the display to display the aligned plurality of second thumbnail images, and wherein the at least one second time point is one of the second time points.

15. The apparatus of claim 10, wherein the controller is further configured to generate the control signal so that at least one of the images showing the portion of the body marker is displayed to be distinguished from the plurality of first thumbnail images and the plurality of second thumbnail images.

16. The apparatus of claim 10, wherein the controller is further configured to measure a parameter of the ROI based on one of the first images, and select, from the stored images of the plurality of objects, images on which the parameter is measured, as the second images.

17. The apparatus of claim 10, wherein the first images are generated under a first condition, and wherein the controller is further configured to select, from the stored images of the plurality of objects, images generated under the first condition, as the second images.

* * * * *